United States Patent
Han

(10) Patent No.: US 11,166,641 B2
(45) Date of Patent: *Nov. 9, 2021

(54) DYNAMICALLY RECONFIGURABLE APERTURES FOR OPTIMIZATION OF PPG SIGNAL AND AMBIENT LIGHT MITIGATION

(71) Applicant: Apple Inc., Cupertino, CA (US)

(72) Inventor: Chin San Han, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 16/123,183

(22) Filed: Sep. 6, 2018

(65) Prior Publication Data

US 2019/0015000 A1 Jan. 17, 2019

Related U.S. Application Data

(63) Continuation of application No. 15/139,133, filed on Apr. 26, 2016, now Pat. No. 10,117,587.

(Continued)

(51) Int. Cl.
*A61B 5/024* (2006.01)
*A61B 5/00* (2006.01)
*A61B 5/1455* (2006.01)

(52) U.S. Cl.
CPC ...... *A61B 5/02427* (2013.01); *A61B 5/14552* (2013.01); *A61B 5/681* (2013.01);
(Continued)

(58) Field of Classification Search
CPC .............. A61B 5/0059; A61B 5/02416; A61B 5/02427; A61B 5/02433; A61B 5/02438;
(Continued)

(56) References Cited

U.S. PATENT DOCUMENTS 5,140,990 A 8/1992 Jones et al.
5,299,570 A * 4/1994 Hatschek
(Continued)

FOREIGN PATENT DOCUMENTS

CN 1503644 6/2004
CN 103610467 3/2014
(Continued)

OTHER PUBLICATIONS

International Search Report dated Aug. 10, 2016, for PCT Application No. PCT/2016/029387, filed Apr. 26, 2016, six pages.
(Continued)

*Primary Examiner* — Eugene T Wu
(74) *Attorney, Agent, or Firm* — Brownstein Hyatt Farber Schreck, LLP

(57) ABSTRACT

This relates to an electronic device with dynamically reconfigurable apertures to account for different skin types, usage conditions, and environmental conditions and methods for measuring the user's physiological signals. The device can include one or more light emitters, one or more light sensors, and a material whose optical properties can be changed in one or more locations to adjust the optical path and the effective separation distances between the one or more light emitters and one or more light sensors or the size, location, or shape of the one or more dynamically reconfigurable apertures. In some examples, the material can be a liquid crystal material, MEMS shutter layer, or light guide, which can form the one or more dynamically reconfigurable apertures. In some examples, the light emitters or light sensors or both can be an array of individually addressable optical components.

19 Claims, 18 Drawing Sheets

Related U.S. Application Data

(60) Provisional application No. 62/153,445, filed on Apr. 27, 2015.

(52) U.S. Cl.
CPC .......... *A61B 5/6898* (2013.01); *A61B 5/7214* (2013.01); *A61B 2560/0252* (2013.01); *A61B 2562/0238* (2013.01); *A61B 2562/0242* (2013.01)

(58) Field of Classification Search
CPC ................ A61B 5/02444; A61B 5/681; A61B 5/6824; A61B 5/6898; A61B 2562/0233; A61B 2562/0238; A61B 2562/0242
See application file for complete search history.

(56) References Cited

U.S. PATENT DOCUMENTS

| | | | |
|---|---|---|---|
| 5,483,261 | A | 1/1996 | Yasutake |
| 5,488,204 | A | 1/1996 | Mead et al. |
| 5,596,987 | A | 1/1997 | Chance |
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,663,607 | B2 | 2/2010 | Hotelling et al. |
| 8,479,122 | B2 | 7/2013 | Hotelling et al. |
| 8,938,279 | B1* | 1/2015 | Heaton |
| 9,498,158 | B2* | 11/2016 | Isaacson |
| 9,739,663 | B2 | 8/2017 | Haider et al. |
| 10,117,587 | B2 | 11/2018 | Han |
| 2004/0111035 | A1 | 6/2004 | Kondoh et al. |
| 2006/0197753 | A1 | 9/2006 | Hotelling |
| 2006/0258922 | A1* | 11/2006 | Mason |
| 2008/0275322 | A1* | 11/2008 | Kim |
| 2010/0331640 | A1* | 12/2010 | Medina |
| 2012/0019713 | A1 | 1/2012 | Gudlavalleti et al. |
| 2013/0046192 | A1 | 2/2013 | Lin et al. |
| 2013/0131519 | A1 | 5/2013 | LeBoeuf et al. |
| 2013/0324866 | A1 | 12/2013 | Gladshtein |
| 2014/0183342 | A1 | 7/2014 | Shedletsky et al. |
| 2016/0058312 | A1 | 3/2016 | Han et al. |
| 2016/0278646 | A1* | 9/2016 | Hu |
| 2016/0296174 | A1* | 10/2016 | Isikman |

FOREIGN PATENT DOCUMENTS

| | | |
|---|---|---|
| JP | 2000-163031 A | 6/2000 |
| JP | 2002-342033 A | 11/2002 |
| WO | WO-2015/056007 A1 | 4/2015 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Non-Final Office Action dated Nov. 1, 2017, for U.S. Appl. No. 15/139,133, filed Apr. 26, 2016, fourteen pages.

Notice of Allowance dated Jul. 5, 2018, for U.S. Appl. No. 15/139,133, filed Apr. 26, 2016, seven pages.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner

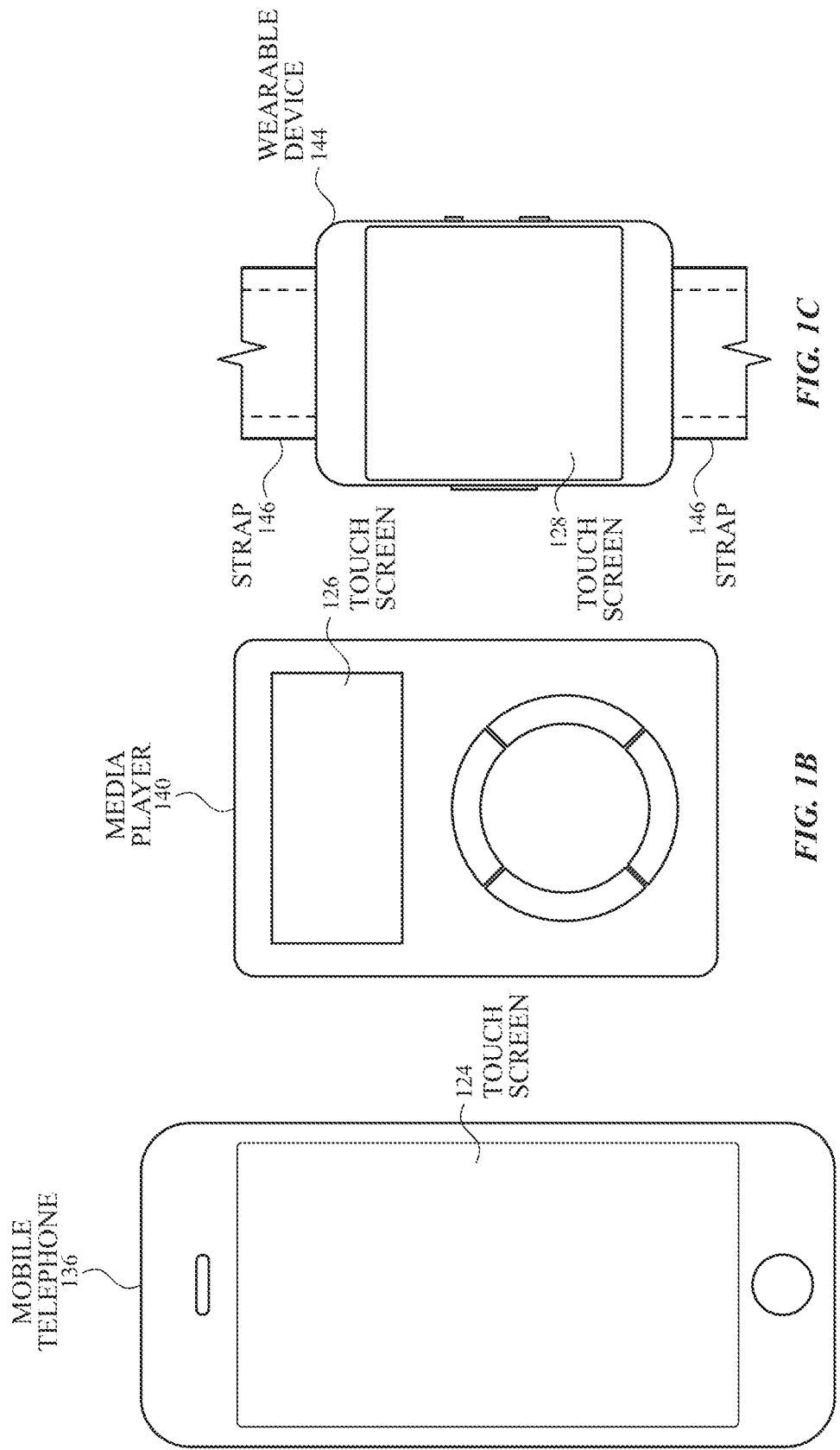

| LIGHT PATH | LIGHT EMITTER | LIGHT SENSOR | PATH LENGTH (MM) | PPG SIGNAL | PERFUSION INDEX |
|---|---|---|---|---|---|
| 555 | 516 | 504 | 4.944 | 1.11 | 0.96 |
| 551 | 506 | 514 | 5.444 | 0.75 | 1.10 |
| 553 | 506 | 504 | 5.915 | 0.51 | 1.23 |
| 557 | 516 | 514 | 6.543 | 0.31 | 1.39 |

DYNAMICALLY RECONFIGURABLE APERTURES FOR OPTIMIZATION OF PPG SIGNAL AND AMBIENT LIGHT MITIGATION

CROSS-REFERENCE TO RELATED APPLICATIONS

This application is a continuation of and claims the benefit of U.S. patent application Ser. No. 15/139,133, filed Apr. 26, 2016 and published on Oct. 27, 2016 as U.S. Patent Publication No. 2016-0310027-A1. U.S. patent application Ser. No. 15/139,133 claims the benefit of U.S. Provisional Application No. 62/153,445, filed Apr. 27, 2015. The contents of U.S. patent application Ser. No. 15/139,133 and Ser. No. 62/153,445 are hereby incorporated by reference in its entirety for all purposes.

FIELD

This relates generally to a device that measures a photoplethysmogram (PPG) signal, and, more particularly, to dynamically reconfigurable apertures for optimization of the PPG signal and ambient light mitigation.

BACKGROUND

A photoplethysmogram (PPG) signal can be measured by PPG systems to derive corresponding physiological signals (e.g., pulse rate). In a basic form, PPG systems can employ a light source or light emitter that emits light through an aperture into the user's tissue. In addition, a light detector can be included to receive light through an aperture that reflects off and exits the tissue. However, determination of the user's physiological signals can be erroneous due to variations in the user's skin type, usage conditions, and environmental conditions affecting the signal of the reflected light.

For a given light emitter and light detector, the PPG signal can decrease as the separation distance between the light emitter and light detector increases. On the other hand, perfusion index can increase as the separation distance between the light emitter and light detector increases. Therefore, shorter separation distances between a light emitter and a light sensor can favor high PPG signal strength, while longer separation distances can favor high perfusion index values (e.g., motion performance). Additionally, the size of the light emitter and/or light detector apertures can lead to insufficient PPG signal strength and/or excessive ambient light intrusion that can introduce noise into the signal and can saturate the signal. Both insufficient PPG signal strength and excessive ambient light intrusion can lead to erroneous measurements. Furthermore, the location or shape (or both) of the apertures may not account for variations in the user's skin that can negatively impact the measurements. While certain architectures, such as multiple path length architectures, can be employed to alleviate these issues, the path lengths and aperture sizes, locations, or shapes cannot be adjusted once the device is manufactured. To account for different skin types, usage conditions, and environmental conditions, a device with dynamically reconfigurable apertures may be needed.

SUMMARY

This relates to an electronic device with dynamically reconfigurable apertures to account for different skin types, usage conditions, and environmental conditions. The user's physiological signals can be measured with one or more light emitters and one or more light sensors. The device can include a material whose optical properties can be changed in one or more locations to adjust the optical path and the effective separation distance between one or more light emitters and one or more light sensors or the size, location, or shape of one or more dynamically reconfigurable apertures. In some examples, the material can be a liquid crystal material, MEMS shutter layer, or light guide, which can form the dynamically reconfigurable apertures. In some examples, the light emitters or light sensors or both can be an array of individually addressable optical components, where the selection or addressing of active optical components can change the properties of the light emitted towards the user's skin and the light reflected off the user's skin, vasculature, and/or blood that is received by the light sensors. In some examples, the device can include multiple light emitters or multiple light sensors or both with different emission or sensing wavelengths.

This also relates to methods for measuring the user's physiological signals. In some examples, a longer separation distance between the light emitter and light sensor can be used for PPG signal measurements, whereas a shorter separation distance can be used for perfusion index measurements. In some examples, the aperture sizes can be adjusted to account for the amount of noise, such as the amount of ambient light intrusion, introduced into the signal. In some examples, the location or shape of an aperture can be adjusted to account for variations in the user's skin. Examples of the disclosure include methods to optimize the properties of the dynamically reconfigurable apertures. These methods can include comparing the signal values of three (or more) configurations and selecting the configuration with the highest (or lowest) signal value. These methods can also include incrementally adjusting the properties of the apertures in a direction with the highest (or lowest) signal value.

BRIEF DESCRIPTION OF THE DRAWINGS

FIGS. 1A-1C illustrate systems in which examples of the disclosure can be implemented.

DETAILED DESCRIPTION

Figure 2A:
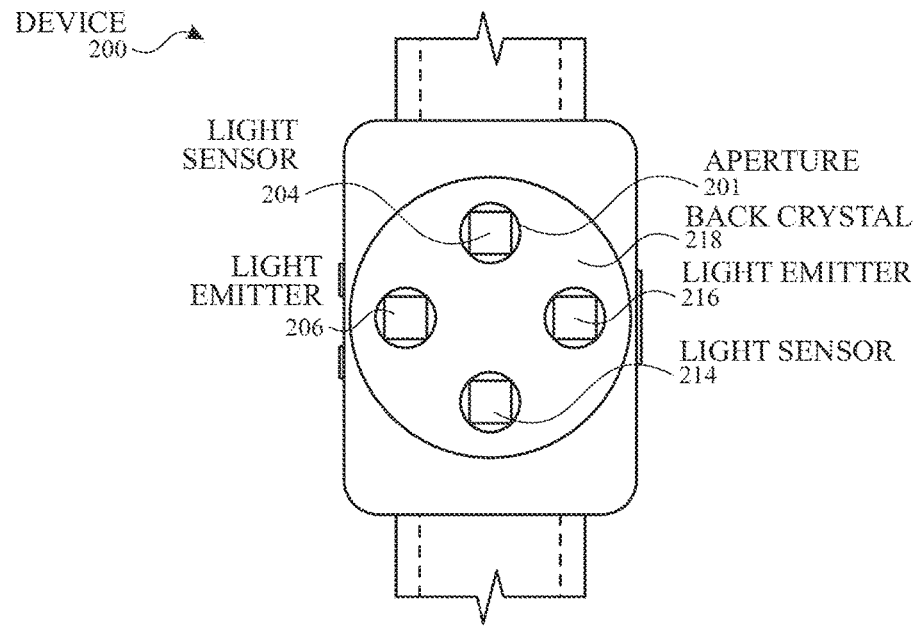
FIG. 2A illustrates a top view of an exemplary electronic device including light sensors and light emitters for measuring a PPG signal according to examples of the disclosure.

In the following description of examples, reference is made to the accompanying drawings in which it is shown by way of illustration specific examples that can be practiced. It is to be understood that other examples can be used and structural changes can be made without departing from the scope of the various examples. Numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

A photoplethysmographic (PPG) signal can be measured by PPG systems to derive corresponding physiological signals (e.g., pulse rate). Such PPG systems can be designed to be sensitive to changes in a user's tissue that can result from fluctuations in the amount or volume of blood or blood oxygen in the vasculature of the user. In a basic form, PPG systems can employ a light source or light emitter that emits light through an aperture into the user's tissue, and a light sensor to receive light that reflects and/or scatters and exits the tissue through another aperture. The PPG signal is the amplitude of reflected and/or scattered light that is modulated with volumetric change in blood volume in the tissue. However, in some examples, some of the reflected and/or scattered light can be lost, leading to a PPG signal measured by the light sensor having a low signal strength. Additionally, the PPG signal can be distorted by noise due to artifacts. Artifacts can result from, for example, the user's movement or ambient light intrusion that can saturate or degrade the signal by introducing noise into the signal. As a result, it can be difficult to accurately determine the user's physiological state.

This disclosure relates to an electronic device with dynamically reconfigurable apertures to account for different skin types, usage conditions (e.g., sedentary, active motion, etc.), and environmental conditions (e.g., indoors, outdoors, etc.). The user's physiological signals can be measured with one or more light emitters and one or more light sensors. The device can include a material whose optical properties can be changed in one or more locations to adjust the optical path and the effective separation distances between the one or more light emitters and one or more light sensors or the size, location, or shape of the one or more dynamically reconfigurable apertures. In some examples, the material can be a liquid crystal material, MEMS shutter layer, or light guide, which can form the one or more dynamically reconfigurable apertures. In some examples, the light emitters or light sensors or both can be an array of individually addressable optical components, where selection of the active optical components can change the properties of the light emitted towards the user's skin and the light reflected off the user's skin, vasculature, and/or blood. In some examples, the device can include multiple light emitters or multiple light sensors or both with different emission or sensing wavelengths.

This disclosure also relates to method for measuring the user's physiological signals. In some examples, a longer separation distance between the light emitter and light sensor can be used for PPG signal measurements, whereas a shorter separation distance can be used for perfusion index measurements. In some examples, the aperture size can be adjusted to account for the amount of noise, such as the amount of ambient light intrusion, introduced into the signal. In some examples, the location or shape of an aperture can be adjusted to account for differences in the user's skin. Examples of the disclosure can include methods to optimize the properties of the dynamically reconfigurable apertures. These methods can include comparing the signal values of three (or more) configurations and selecting the configuration with the highest (or lowest) signal value. These methods can also include incrementally adjusting the properties of the apertures toward a direction and/or size with the highest (or lowest) signal value.

Representative applications of the apparatus and methods according to the present disclosure are described in this section. These examples are being provided solely to add context and aid in the understanding of the described examples. It will thus be apparent to one skilled in the art that the described examples may be practiced without some or all of the specific details. Other applications are possible, such that the following examples should not be taken as limiting.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the reconfigurable apertures and methods for detecting a PPG signal as will be disclosed.

Figure 2B:
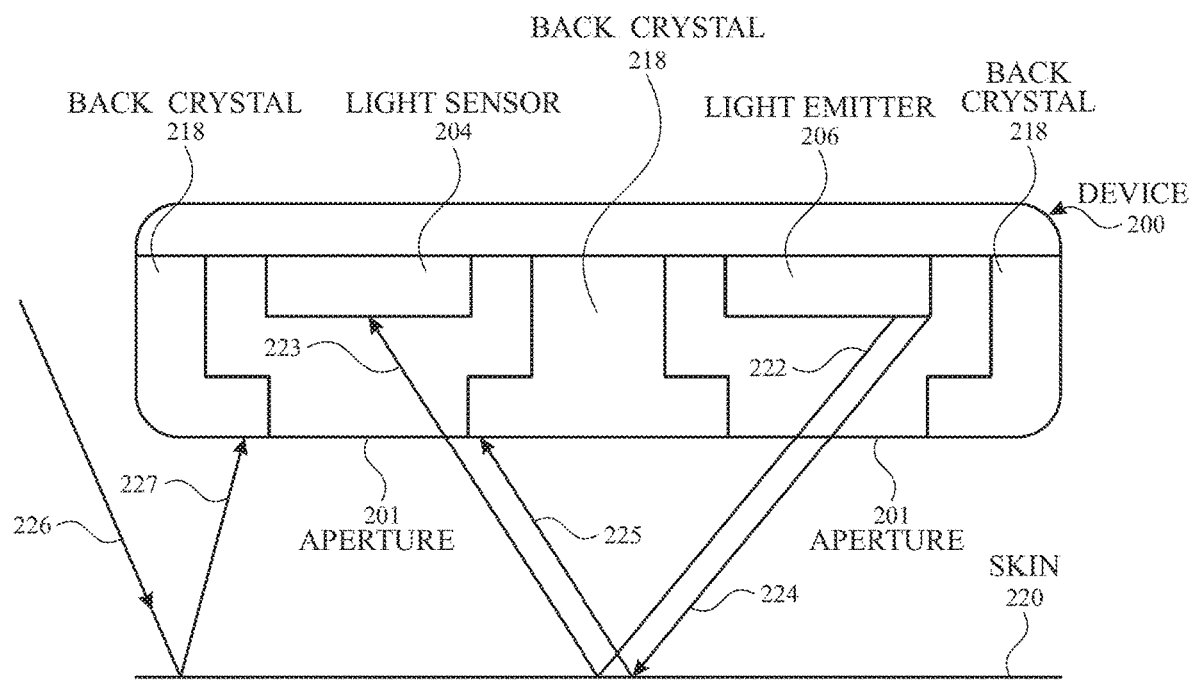
FIG. 2B illustrates a cross-sectional view of an exemplary electronic device including light sensors and light emitters for measuring a PPG signal according to examples of the disclosure.

FIG. 2A illustrates a top view and FIG. 2B illustrates a cross-sectional view of an exemplary electronic device including light sensors and light emitters for measuring a PPG signal according to examples of the disclosure. The top view in FIG. 2A can be viewed as the underside of wearable device 144 of FIG. 1C, for example. A light sensor 204 can be located proximate to a light emitter 206 on a surface of device 200. Additionally, another light sensor 214 can be located or paired with light emitter 216 on a surface of device 200. Device 200 can be situated such that light sensors 204 and 214 and light emitters 206 and 216 are proximate to a skin 220 of a user. For example, device 200 can be held in a user's hand or strapped to a user's wrist, among other possibilities.

Light emitter 206 can generate light 222 and 224 exiting aperture 201. Light 222 can be directed towards and incident upon the user's skin 220. A portion of light 222 can be absorbed by skin 220, vasculature, and/or blood, and a portion of light (i.e., light 223) can reflect back for detection by light sensor 204. Light 224 can also be incident upon skin 220, a portion of light 224 can be absorbed by skin 220, vasculature, and/or blood, and a portion of light (i.e., light 225) can reflect back towards device 200. However, light 225 can be incident on back crystal 218 and may not reach light sensor 204. Similarly, ambient light 226 can be incident upon skin 220. A portion of the ambient light (i.e., light 227) can reflect back towards device 200, and light 227 can be absorbed by back crystal 218.

Figure 2C:
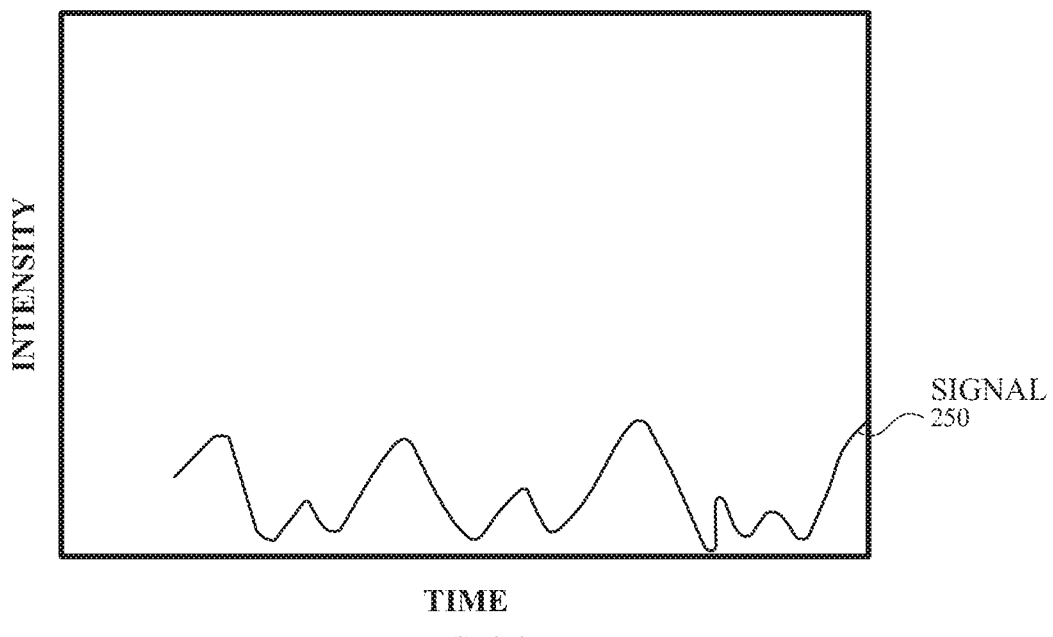
FIG. 2C illustrates a signal detected by a light sensor in PPG system according to examples of the disclosure.

FIG. 2C illustrates a signal detected by a light sensor for determining the user's physiological state in an exemplary electronic device according to examples of the disclosure. Signal 250 can be a low intensity signal measured by light sensor 204. The intensity of signal 250 can be low because the size, shape, or location of aperture 201 can block a portion of the reflected light, such as light 225, and prevent the light from being incident on the active area of the light sensors, such as light sensor 204. Such a signal may be too low for accurate determination of the user's physiological state. While the intensity of the detected signal 250 can be increased by increasing the intensity of light generated from light emitter 206, such a solution may not be feasible especially in portable or compact-sized electronic devices, whose power consumption can be limited due to portability and size requirements.

Figure 3A:
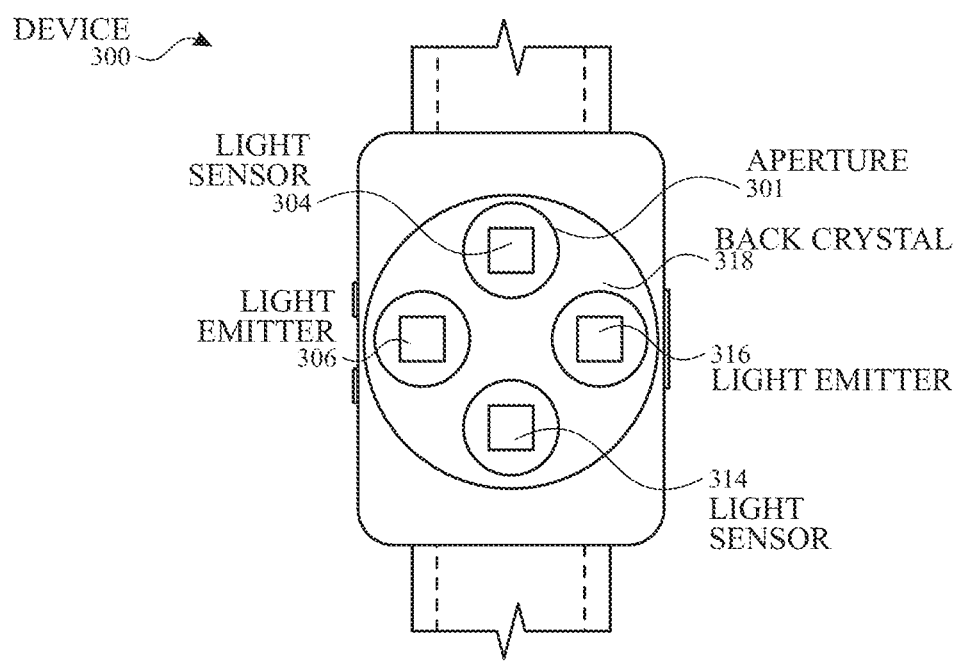
FIG. 3A illustrates a top view of an exemplary electronic device including light sensors and light emitters with increased aperture sizes for measuring a PPG signal according to examples of the disclosure.
Figure 3B:
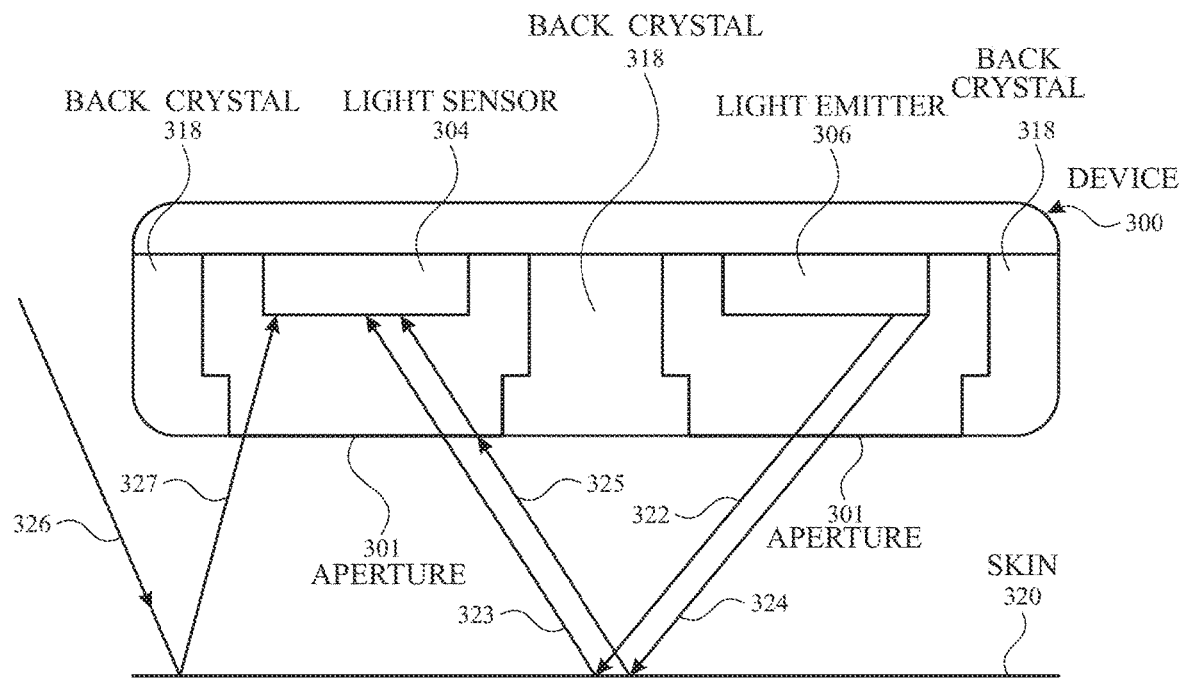
FIG. 3B illustrates a cross-sectional view of an exemplary electronic device including light sensors and light emitters with increased aperture sizes for measuring a PPG signal according to examples of the disclosure.

One way to overcome or alleviate the problem of having low signal intensity can be to enlarge one or more aperture sizes. FIGS. 3A and 3B illustrate a top view and a cross-sectional view of an exemplary electronic device including light sensors and light emitters with increased aperture sizes for measuring a PPG signal according to examples of the disclosure. Device 300 can include light emitters 306 and 316 and light sensors 304 and 314 located on a surface of device 300. In some examples, either light sensors 304 and 314 or light emitters 306 and 314 or both can be symmetrically placed with respect to the center of the back crystal 318. Light emitters 306 and 316 and light sensors 304 and 314 can be facing towards a user's skin 320. The light emitters 306 and 316 can emit light at and can detect light reflected from the user's skin 320, vasculature, and/or blood by passing through apertures 301.

Light emitter 306 can emit light 322 and 324 through aperture 301 towards skin 320. Both light 322 and 324 can be partially absorbed by skin 320, vasculature, and blood. Light 323 and 325 can represent the portions of light 322 and 324 that are not absorbed by skin 320 and instead, are reflected back towards device 300. Both light 323 and 325 can be detected by light sensor 304 to generate a signal representing the modulated light.

Each aperture 301 can have a diameter (or area) greater than the diameter (or area) of aperture 201 of FIGS. 2A and 2B. By increasing the aperture sizes, neither light 323 nor 325 is absorbed by back crystal 318, which can lead to measured modulated light values with an increased intensity. The increased intensity can make the signal strength sufficient enough to make detection of the PPG signal realizable, unlike signal 250 illustrated in FIG. 2C. While increasing the aperture sizes can effectively increase the modulated signal strength, the larger apertures may allow unwanted light to pass through to be sensed by light sensor 304. For example, ambient light 326 can reflect off the user's skin 320, enter into aperture 301, and can reach the active area of the light sensor 304. Ambient light can also directly enter into the aperture and onto the light sensor without striking the user's skin. With an increase in the ambient light 327 reaching the active area of the light sensor 304, the unmodulated signal intensity can increase. An increase in unmodulated signal intensity can cause the perfusion index to decrease and the signal-to-noise ratio to decrease.

Figure 3C:
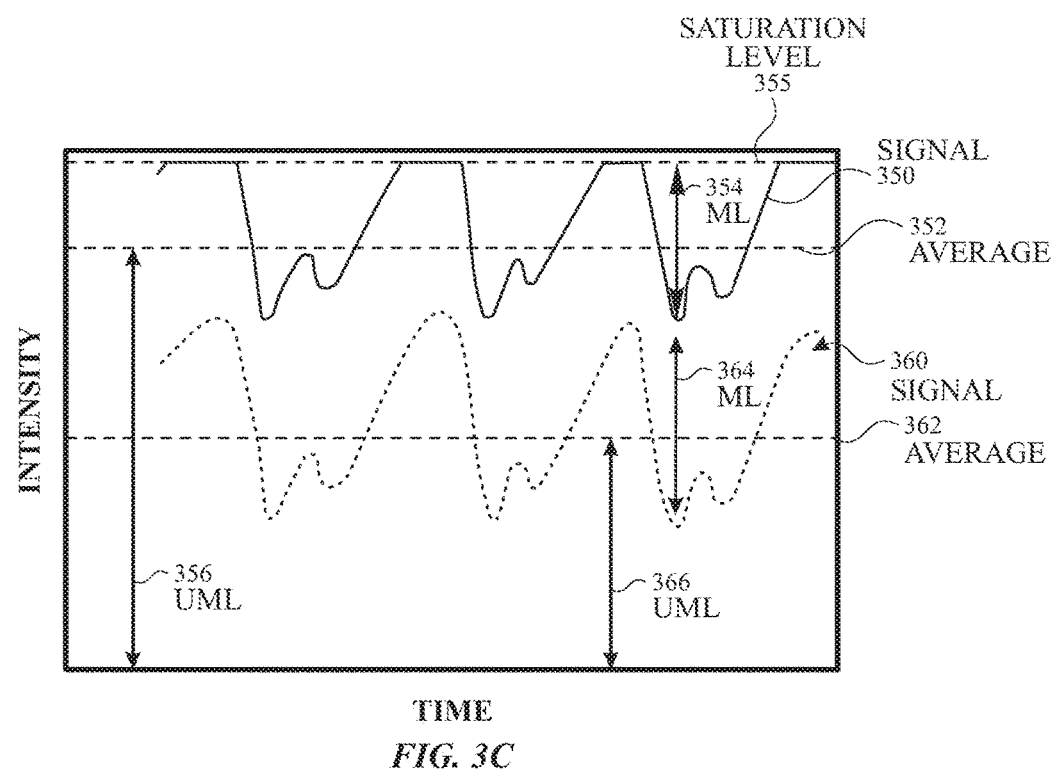
FIG. 3C illustrates a PPG signal and a signal detected by a light sensor with an increased aperture size in an exemplary device according to examples of the disclosure.

FIG. 3C illustrates a signal detected by a light sensor with an increased aperture size used for measuring a PPG signal in an exemplary device according to examples of the disclosure. Signal 350 can be the measured total signal (i.e., sum of the measured modulated light and unmodulated light, including ambient light) detected by light sensor 304. Signal 360 can be the actual PPG signal that accurately represents the user's physiological state.

Device 300 can take the actual PPG signal, such as signal 360, and determine the user's perfusion index. The perfusion index can be the ratio of received modulated light (ML 364) to unmodulated light (UML 366) (i.e., ratio of blood flow modulated signal to static, parasitic DC signal) and can give extra information regarding the user's physiological state. The modulated light (ML) can be the peak-to-valley value, and the unmodulated light (UML) can be the zero-to-average (average 362) value of the PPG signal 360. As shown in FIG. 3C, the perfusion index can be equal to the ratio of ML 364 to UML 366.

Both signals 350 and 360 can have an amplitude that is modulated as a result of pulsatile blood flow (i.e., "signal") and parasitic, unmodulated, non-signal light (i.e., DC). However, the unmodulated light UML 356 of signal 350 can be higher than the unmodulated light UML 366 of signal 360 due to signal 350 including noise. Noise can be generated from motion artifacts, ambient light intrusion (e.g., due to light sensor 304 detecting ambient light 327), or light that has not penetrated a blood layer, for example. The added noise or unmodulated light values can distort the determination of the user's physiological state. This can be particularly true in situations where the unmodulated light can saturate the total signal detected by light sensor 304. For example, as shown in the figure, signal 350 can reach the saturation level 355. As a result, the modulated light ML 354 detected by the light sensor can be lower in value (e.g., truncated), so the PPG signal can be incorrect. Given that the unmodulated light UML 356 can be erroneously high in value (e.g., saturated) and the modulated light ML 354 can be erroneously low in value (e.g., truncated), the perfusion index, being equal to the ratio of ML 354 to UML 356, and the PPG signal may be incorrectly determined.

One way to increase the signal intensity or signal strength without increasing the unmodulated light intensity can be to reduce the distance between light sensors and light emitters such that light travels a shorter distance. Generally, for a given light emitter and light sensor pair, the signal strength decreases with increasing separation distance between the light emitter and the light sensor. On the other hand, the perfusion index generally increases with increasing separation distance between the light emitter and the light sensor. A higher perfusion index can correlate to better rejection of artifacts caused by, for example, motion or ambient light. Therefore, shorter separation distances between a light emitter and a light sensor can favor high PPG signal strength, while longer separation distances can favor high perfusion index. That is, a trade-off can exist, making it difficult to optimize separation distance for particular user skin/tissue types, usage conditions, and environmental conditions.

Figure 4A:
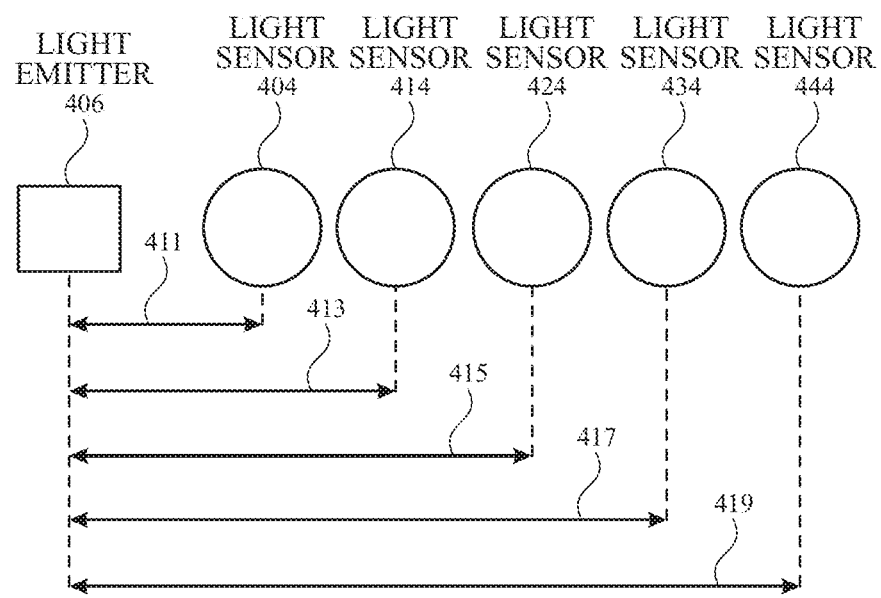
FIGS. 4A-4B illustrate exemplary relationships for the separation distance between a light emitter and a light sensor and the PPG signal and perfusion index according to examples of the disclosure.
Figure 4B:
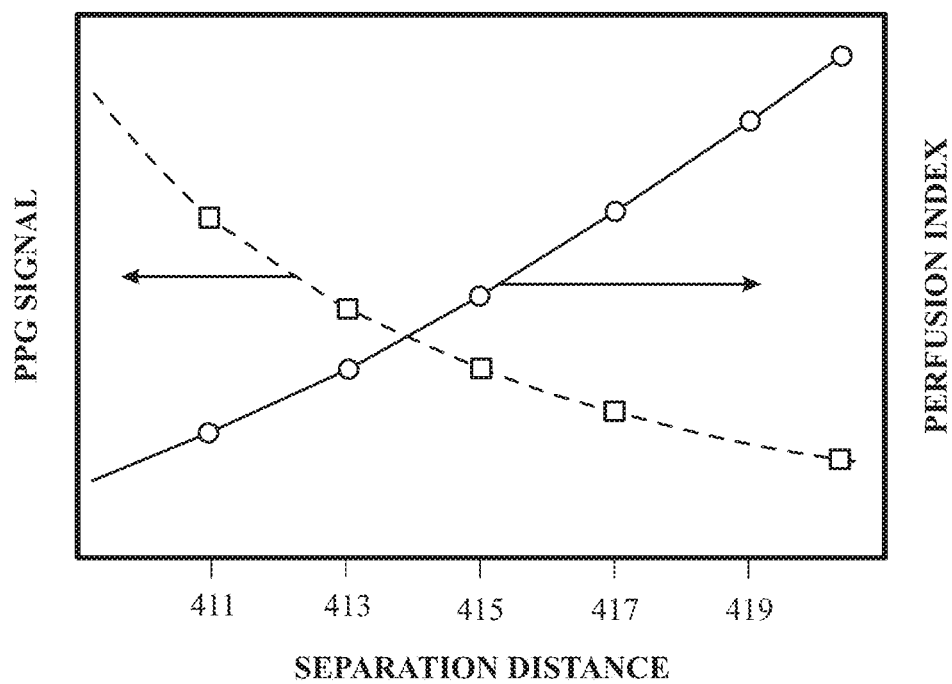

FIGS. 4A-4B illustrate exemplary relationships for the separation distance between a light emitter and a light sensor and the PPG signal and perfusion index according to examples of the disclosure. Light sensor 404 can have a separation distance 411 from light emitter 406. Light sensor 414 can have a separation distance 413 from light emitter 406. Light sensor 424 can have a separation distance 415 from light emitter 406. Light sensor 434 can have a separation distance 417 from light emitter 406. Light sensor 444 can have a separation distance 419 from light emitter 406. Separation distances 411, 413, 415, 417, and 419 can be different. In some examples, the light emitter 406 and light sensors 404, 414, 424, 434, and 444 can be placed directly upon the user's skin, and the separation distances 411, 413, 415, 417, and 419 can be directly correlated to the distance the light travels within the skin. As plotted in FIG. 4B, a shorter separation distance can lead to a lower perfusion index and a higher PPG signal, whereas a longer separation distance can lead to a higher perfusion index and lower PPG signal.

Figure 5A:
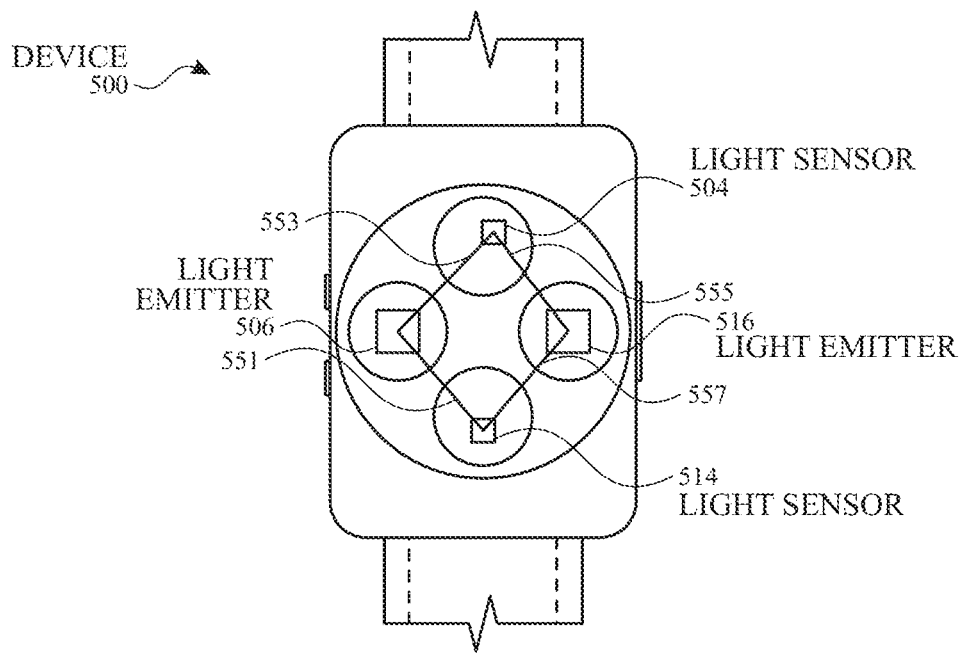
FIG. 5A illustrates a top view of an exemplary device with multiple light paths for measuring a PPG signal according to examples of the disclosure.
Figure 5B:
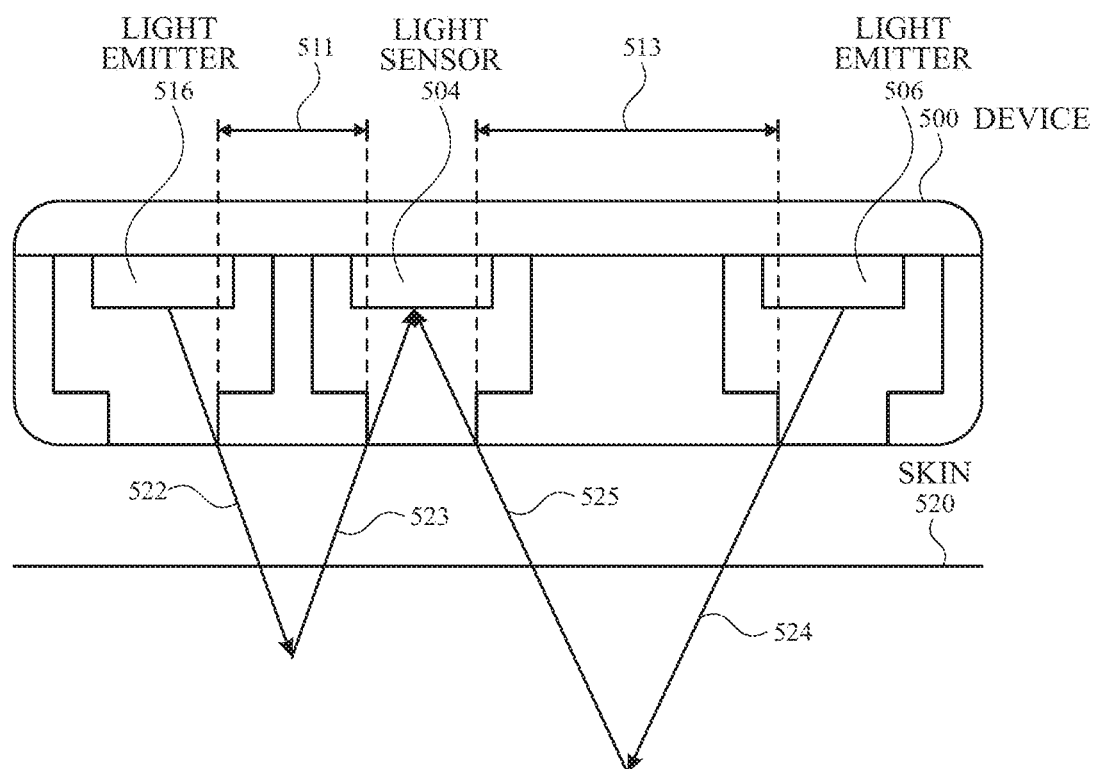
FIG. 5B illustrates a cross-sectional view of an exemplary device with multiple light paths for measuring a PPG signal according to examples of the disclosure.

To alleviate the trade-off issues between signal strength and perfusion index, multiple light paths with various distances between the light emitters and the light sensors can be employed. FIG. 5A illustrates a top view and FIG. 5B illustrates a cross-sectional view of an exemplary device with multiple light paths for determining the user's physiological state according to examples of the disclosure. Device 500 can include light emitters 506 and 516 and light sensors 504 and 514 located on a surface of device 500. The edge of the aperture associated with light emitter 506 can have a separation distance 513 from the edge of the aperture associated with light sensor 504, and the edge of the aperture associated with light emitter 516 can have a separation distance 511 from the edge of the aperture associated with light sensor 504.

Light 522 from light emitter 516 can be incident upon skin 520 and can reflect back as light 523 detected by light sensor 504. Similarly, light 524 from light emitter 506 can be incident upon skin 520 and can reflect back as light 525 detected by light sensor 504. In some examples, light emitters 506 and 516 and light sensor 504 can be placed directly upon the user's skin, and the separation distances 511 and 513 can be directly correlated to the distance the light travels within the skin. Separation distance 511 can be shorter than separation distance 513, and as a result, light 523 can have a higher PPG signal strength than light 525. However, light 525 can have a higher perfusion index than light 523 due to the longer separation distance. In some examples, light 522 and 523 can travel a shorter distance through the skin than light 524 and 525 travels. This shorter distance that light 522 and 523 travel can be associated with the shorter separation distance 511. Similarly, the longer distance that light 524 and 524 travel can be associated with the longer separation distance 513. Light emitter 516 and light sensor 504 can be employed for applications requiring a high PPG signal, whereas light emitter 506 and light sensor 504 can be employed for applications requiring a high perfusion index. Due to the different separation distances 511 and 513, information extracted from light 523 and 525 can provide various combinations of PPG signals and perfusion index values to allow the device to dynamically select light information for particular user skin types, usage conditions, and environmental conditions.

Light emitters 506 and 516 can be symmetrically placed, while light sensors 504 and 514 can be asymmetrically placed. Light emitters 506 and 516 and light detectors 504 and 514 can be arranged such that there are four light paths with four different separation distances, for example. In some examples, a separation distance can be the distance between the edge of an aperture associated with a light emitter and an edge of an aperture associated with a light sensor. Light path 551 can be coupled to light emitter 506 and light sensor 514. Light path 553 can be coupled to light emitter 506 and light sensor 504. Light path 555 can be coupled to light emitter 516 and light sensor 504. Light path 557 can be coupled to light emitter 516 and light sensor 514.

Figures 5C, 6A:
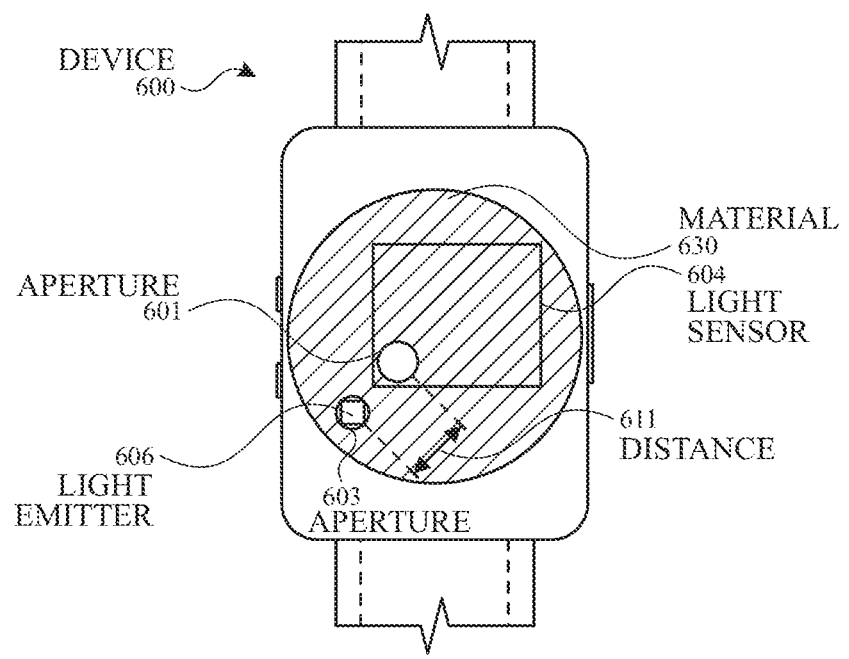
FIG. 5C illustrates a table of exemplary path lengths, relative PPG signal values, and relative perfusion index values for multiple light paths in an exemplary device according to examples of the disclosure.
FIGS. 6A-6B illustrate top views of an exemplary electronic device capable of dynamically adjusting the path length between a light emitter and a light sensor according to examples of the disclosure.

FIG. 5C illustrates a table of exemplary path lengths, relative PPG signals levels, and relative perfusion index values for light paths 551, 553, 555, and 557 of device 500 according to examples of the disclosure. As shown, relative PPG signal levels can be higher for shorter path lengths because there can be less light loss when the light emitter and light sensor are located close together such that light can travel through a shorter distance of the user's skin. For example, light path 555 can have a higher PPG signal of 1.11 than light path 557 with a PPG signal of 0.31 due to the shorter path length (the path length of light path 555 can be 4.944 mm, whereas the path length of light path 557 can 6.543 mm). For applications that require high PPG signal levels, device 500 can favor information from light paths 555 or 551 over information from light paths 553 or 557. However, relative perfusion index values can be higher for longer path lengths because light that travels along a greater distance in the skin can include a higher fraction or percentage of pulsatile signal and a smaller fraction or percentage of parasitic signal. For example, light path 553 can have a higher perfusion index value of 1.23, whereas light path 551 can have a lower perfusion index value of 1.10 due to the longer path length (the path length of light path 553 can be 5.915 mm, whereas the path length of light path 551 can be 5.444 mm). For applications that require high perfusion index values, device 500 can favor information from light path 553 over information from light path 551, for example. While FIG. 5C illustrates exemplary values for path lengths 551, 553, 555, and 557 along with exemplary PPG signal levels and perfusion index values, examples of the disclosure are not limited to these values.

Information obtained from the multiple light paths can be used both for applications requiring a high PPG signal strength and for applications requiring a high perfusion index value. In some examples, information generated from all light paths can be utilized. In some examples, information generated from some, but not all light paths can be utilized. In some examples, the "active" light paths can be dynamically changed based on the application(s), available power, user type, and/or measurement resolution.

Although the path lengths or aperture sizes or both of the one or more exemplary devices disclosed above may be adjusted in consideration of the trade-off between PPG signal and perfusion index, the path lengths and aperture sizes cannot be adjusted once the device has been manufactured. Many users desire a portable electronic device that can be used for multiple activities (i.e., usage conditions) and can be used in a variety of environmental conditions. Additionally, the skin types can vary from user to user, so a device that has fixed path lengths and aperture sizes may have limited capabilities. For example, the melanin content can vary significantly from user to user. The skin of a user with high melanin content can absorb a large amount of emitted light from the light emitter, so less light can reflect and/or scatter back towards the light sensor. As a result, a device that can favor a high PPG signal over perfusion index can be desirable only for users with high melanin content, for example. On the other hand, a device may not need to favor a high PPG signal if the user's skin has low melanin content. Usage conditions can also vary. For example, a user can be exercising or engaging in high movement activities. A device that can sacrifice a high PPG signal and can favor a high perfusion index for reducing the motion artifacts can be desired, but only for the time when the user is active. Furthermore, environmental conditions can vary. For example, the device can be located outdoors under sunny conditions. A device that can account for ambient light intrusion and can prevent the ambient light from saturating the signal can be desired. If the user and the device move to an indoor location with low ambient light levels, a device that can account for the change in ambient light without compromising signal level can be desired. In some examples, the temperature of the environment can cause a change in the blood volume in the user's skin surface. A lower blood volume due to a colder temperature environment can require additional light power to obtain the PPG signal, for example. To account for the different skin types, usage conditions, and environmental conditions, a device with dynamically reconfigurable apertures may be needed.

Figure 6B:
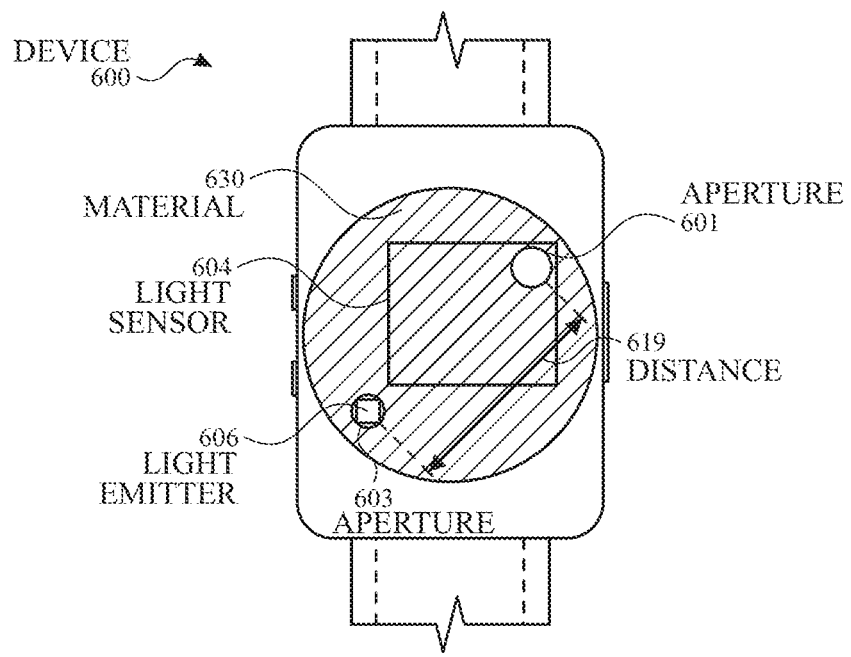

FIGS. 6A-6B illustrate top views of an exemplary electronic device capable of dynamically adjusting the path length between a light emitter and a light sensor according to examples of the disclosure. Device 600 can include a light emitter 606 and a light sensor 604. Device 600 can optionally include an optical isolation (not shown) to prevent direct optical cross talk between the light emitter 606 and light sensor 604. Light emitter 606 can be any type of light source, including but not limited to, light emitting diodes (LEDs), incandescent lights, fluorescent lights, organic light emitting diodes (OLEDs), and electroluminescent diodes (ELDs). Light sensors 604 can be any type of optical sensing device such as a photodiode. In some examples, light emitter 606 and light sensor 604 can be fixed in location. Aperture 603 can be located above light emitter 606 such that light emitted from light emitter 606 can transmit through aperture 603. Aperture 601 can be located above light sensor 604 such that light entering aperture 601 can transmit through and be incident upon the active area of light sensor 604. Device 600 can further include material 630 located above light sensor 604, light emitter 606, or both. In some examples, material 630 can be opaque, and apertures 601 and 603 can be transparent. In some examples, the optical properties of material 630 can be dynamically adjusted or can vary amongst different locations or both. For example, material 630 can block light (can be opaque) in one or more locations (e.g., areas outside of apertures 601 and 603), while transmitting light (can be transparent) in one or more locations (e.g., apertures 601 and 603). Although the figure illustrates only one light emitter and only one light sensor, examples of the disclosure can include a device with multiple light emitters or multiple light sensors or both.

The distance or path length between the light sensor 604 and light emitter 606 can be dynamically adjusted. As shown in FIG. 6A, the properties of material 630 can change such that aperture 601 can be located a distance 611 away from light emitter 606. As shown in FIG. 6B, the properties of material 630 can be adjusted such that aperture 601 can be located a distance 619 away from light emitter 606. In both figures, the light emitter 606 and light sensor 604 can remain in the same location. Additionally, apertures 601 and 603 can retain their shape and size.

Figure 6C:
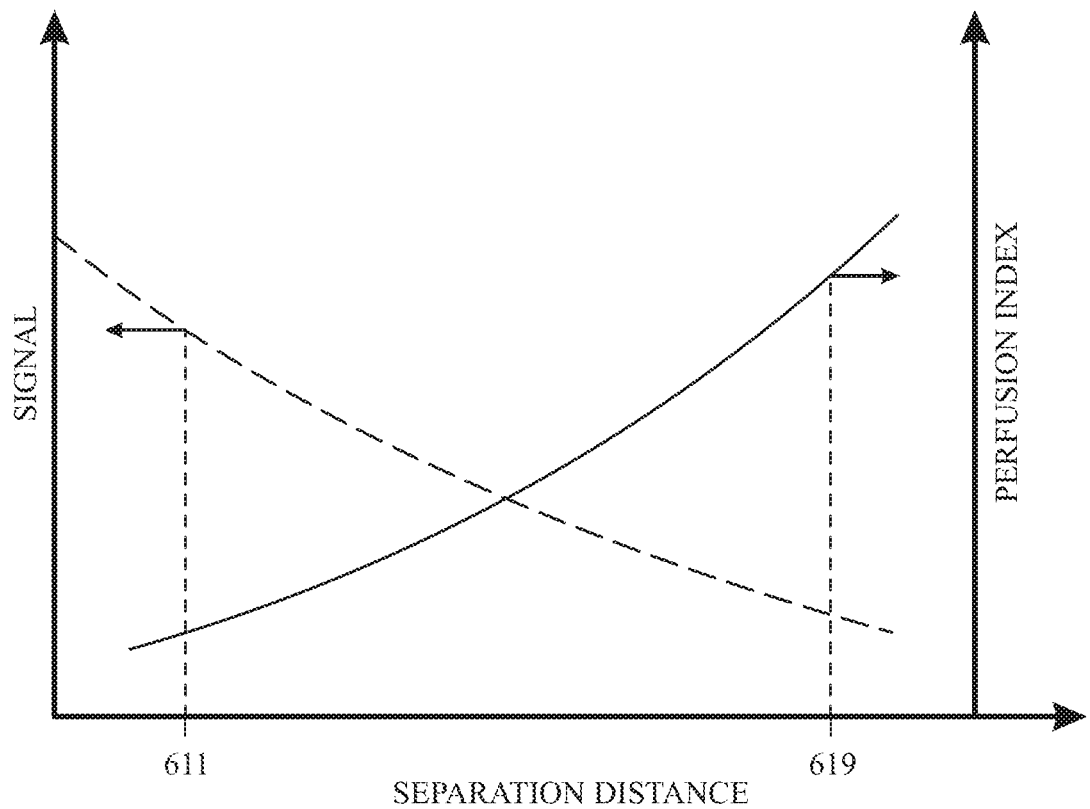
FIG. 6C illustrates an exemplary relationship for two apertures with different separation distances and the corresponding PPG signal and perfusion index according to examples of the disclosure.

At an instance in time, a high PPG signal can be detected when apertures 601 and 603 are located the shorter distance 611 away from each other, as shown in FIG. 6A. At another instance in time, a high perfusion index can be detected when apertures 601 and 603 are located the longer distance 619 away from each other, as shown in FIG. 6B. In some examples, device 600 can change the location of the aperture based on the amount of ambient light detected. For example, if the amount of ambient light detected through an aperture at a first location exceeds a threshold value, the device can relocate the aperture to a second location, different from the first location, where the ambient light value can be less than the threshold value in the second location. In some examples, the second location can be further away from the ambient light source then the first location. By dynamically adjusting the location of apertures 601 and 603 relative to each other through a change in the optical properties of material 630, both a high PPG signal and a high perfusion index can be achieved, as illustrated in FIG. 6C.

Figure 6D:
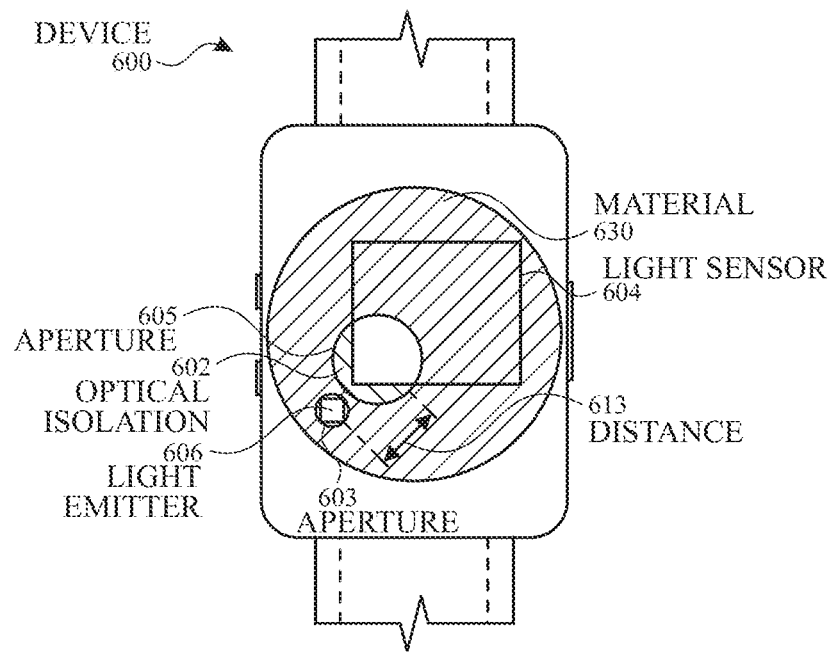
FIGS. 6D-6E illustrate top views of an exemplary electronic device capable of dynamically adjusting the aperture size according to examples of the disclosure.
Figure 6E:
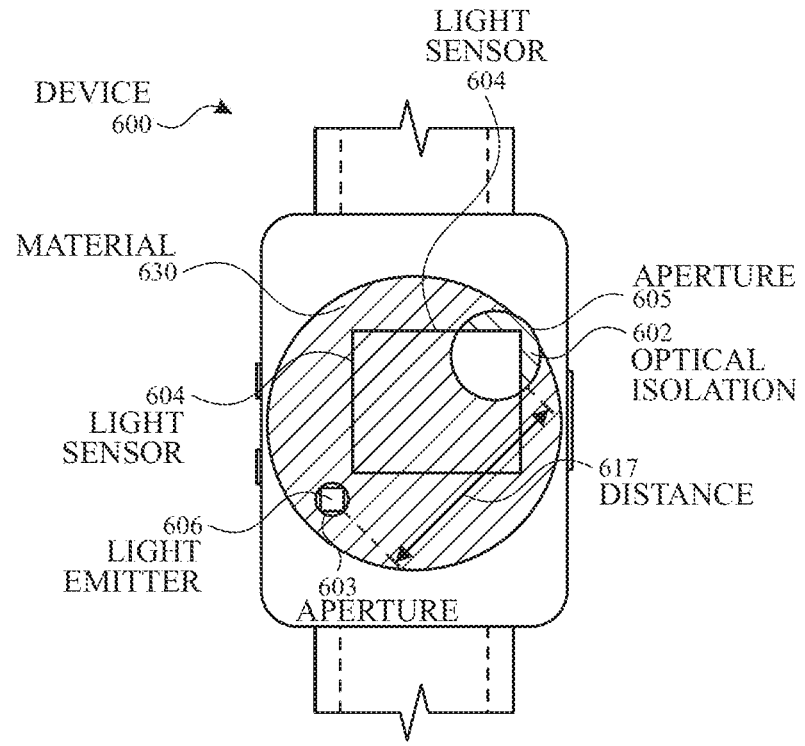

In addition to adjusting the path length, the aperture size can be adjusted. FIGS. 6D-6E illustrate top views of an exemplary electronic device capable of dynamically adjusting the aperture size according to examples of the disclosure. Device 600 can include a light emitter 606 and an aperture 603 located above light emitter 606 such that light emitted from light emitter 606 can transmit through aperture 603. Device 600 can also include light sensor 604 and an aperture 605 located above light sensor 604 such that light entering aperture 605 can transmit through and be incident upon the active area of light sensor 604. In some examples, apertures 603 and 605 can be formed through one or more dynamic changes in the optical properties of material 630. In some examples, material 630 can be transparent in the same locations as aperture 603 and 605. In some examples, material 630 can be opaque in one or more areas located outside of apertures 603 and 605.

Figure 6F:
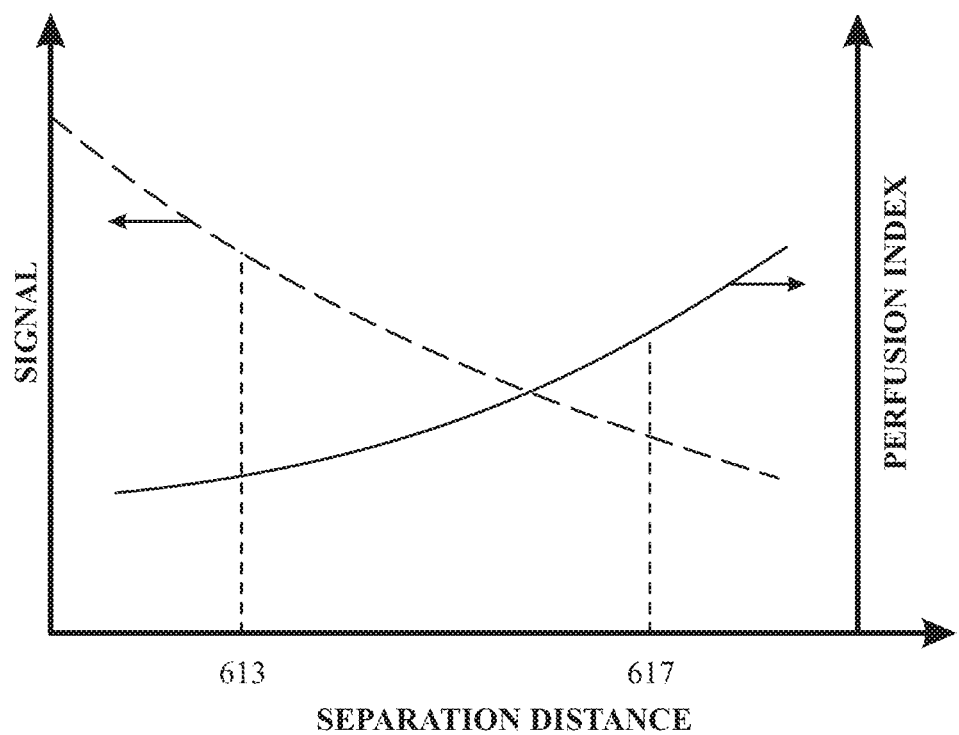
FIG. 6F illustrates an exemplary relationship for two apertures of increased size with different separation distances and the corresponding PPG signal and perfusion index according to examples of the disclosure.

As illustrated in FIG. 6D, a PPG signal or perfusion index or both can be determined by locating apertures 603 and 605 with a separation distance 613. Aperture 605 can be relocated such that the separation distance between apertures 603 and 605 changes to separation distance 617, as illustrated in FIG. 6E. In some examples, separation distance 613 can be shorter than separation distance 617. In this manner, a high PPG signal can be measured when apertures 603 and 605 are located the shorter distance 613 apart, and a high perfusion index can be measured when apertures 603 and 605 are located the longer distance 617 apart. Device 600 can obtain both an accurate PPG signal and perfusion index, as illustrated in FIG. 6F, by using the same optical components.

Device 600 can have fewer optical components for multiple path length measurements. Compared to device 500 of FIG. 5A where four different optical components (e.g., light sensors 504 and 514 and light emitters 506 and 516) were needed to generate four different path lengths (e.g., lengths associated with paths 551, 553, 555, and 557), device 600 may need only two optical components (e.g., light sensor 604 and light emitter 606) to generate four different path lengths (e.g., distances 611, 613, 617, and 619). Fewer optical components can lead to not only lower costs and more compact devices, but also the optical sensing capabilities can be enhanced. The optical sensing capabilities can be enhanced because the size of the optical components may not be constrained or "crowded," and there can be a lower likelihood for optical crosstalk. Device 600 can also include an optical isolation 602 to prevent direct optical cross talk between the light emitter 606 and light sensor 604.

Not only can one or more path lengths or separation distances be dynamically adjusted, but also one or more aperture sizes can be dynamically adjusted. For example, aperture 601 (illustrated in FIGS. 6A-6B) can have a different size or area than aperture 605 (illustrated in FIGS. 6D-6E). In some examples, aperture 605 can have an area $A_2$, greater than the area $A_1$ of aperture 601. In some examples, device 600 can make two or more adjustments to the size or area of the aperture. For example, device 600 can have an aperture 609 with an area $A_3$, greater than both $A_1$ and $A_2$, as illustrated in FIG. 6G.

The device can change one or more aperture sizes for any number of reasons. For example, if the device determines that a higher intensity modulated light is desired or needed, the device can increase one or more aperture sizes. In some examples, the device can determine that ambient light is saturating the signal, so the device can reduce one or more aperture sizes. FIG. 6I shows a plot illustrating the effect aperture area has on signal intensity and ambient light intrusion according to examples of the disclosure. As the aperture area increases, the signal intensity increases. However, the trade-off to a higher signal intensity can be higher ambient light intrusion, which can distort the detected signal. Since the relative signal intensity to ambient light intrusion can vary depending on many factors, such as the user's skin type, usage conditions, and environmental conditions, a device with one or more fixed aperture areas may limit the accuracy of the PPG signal and perfusion index.

In some examples, the device can adjust the aperture size based on a calibration procedure custom tailored to the user's skin type or the location on the user's skin that the device is attached to, held with, or touching. In some examples, the device can adjust the aperture size based on the type of desired measurement(s) or the application.

Figure 6G:
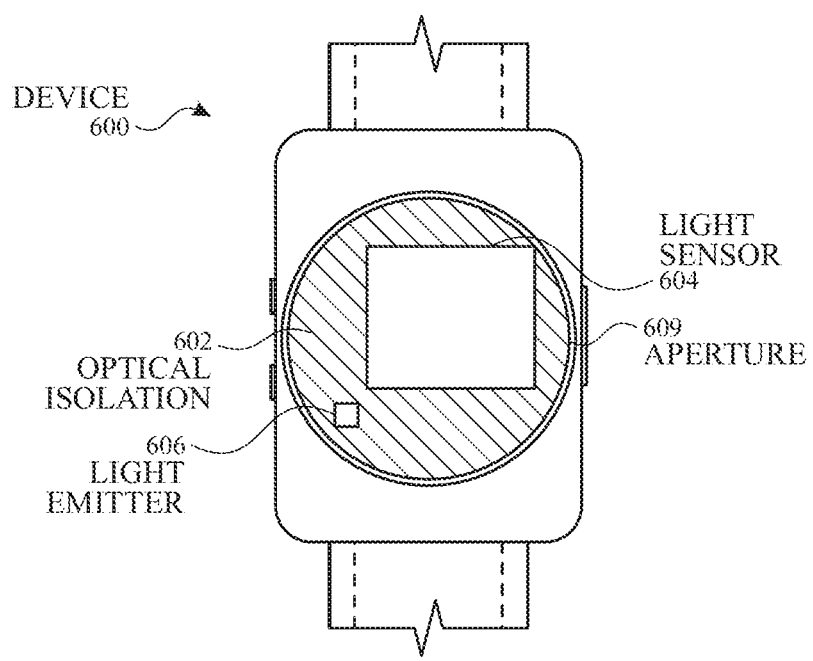
FIGS. 6G-6H illustrate top views of an exemplary electronic device capable of dynamically adjusting the number of apertures according to examples of the disclosure.
Figure 6H:
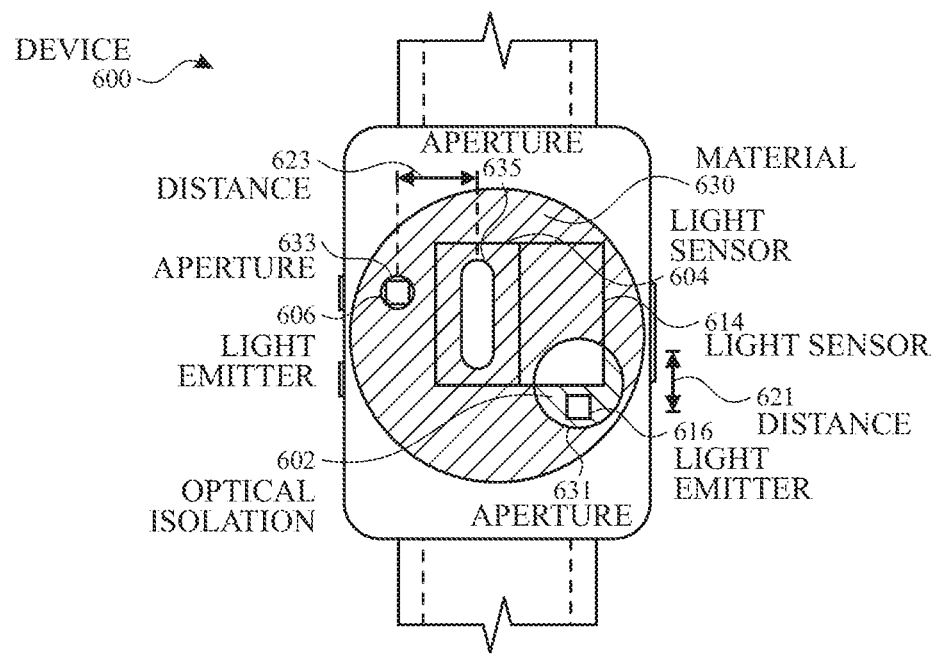
Figure 6I:
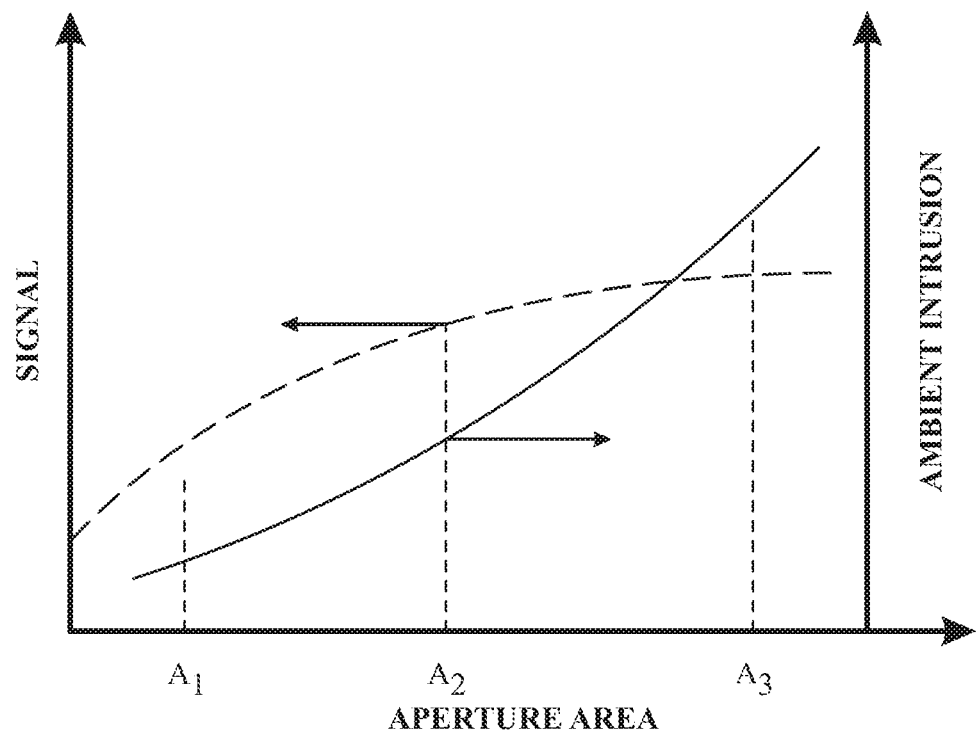
FIG. 6I illustrates an exemplary relationship between aperture area and the PPG signal and perfusion index according to examples of the disclosure.

In some examples, the number of apertures can by dynamically adjusted, as illustrated in FIGS. 6G-6H. Device 600, as illustrated in FIG. 6G, can include one aperture 609. Aperture 609 can allow light emitted from light emitter 606 to transmit through to the user's skin (not shown), and the same aperture 609 can allow light reflected and/or scattered from the user's skin to transmit through to be detected by light sensor 604. In some examples, the size of aperture 609 can be such that the active areas of both light emitter 609 and light sensor 604 are exposed to the user's skin.

FIG. 6H illustrates a top view of an exemplary electronic device including multiple apertures and multiple optical components according to examples of the disclosure. Device 600 can include light emitters 606 and 616, light sensors 604 and 614, and material 630. Material 630 can be configured with multiple apertures 631, 633, and 635. Aperture 631 can be associated or coupled with both light emitter 616 and light sensor 614. Aperture 633 can be associated with light emitter 606, and aperture 635 can be associated with light sensor 604. Aperture 633 can be located a separation distance 623 away from aperture 635. Light emitted from light emitter 616 and exiting aperture 631 can be located a separation distance 621 away from light entering aperture 631 and detected by light sensor 614. In some examples, distances 621 and 623 can be different. In some examples, distance 621 and 623 can be the same. In some examples, light sensors 604 and 614 can be a single detector that is apportioned into two or more sections.

In some examples, light sensor 604 and 615 can be a single large detector, such as light sensor 604 illustrated in FIG. 6G. In a first time period, material 630 can be reconfigured such that light is allowed to transmit through the first aperture (e.g., aperture 631), while preventing light from transmitting through the second aperture (e.g., aperture 635). Light emitter 606 or light emitter 616 or both can be "active" by emitting light whose reflection is captured by aperture 631. In a second time period, material 630 can be reconfigured such that light is allowed to transmit through the second aperture (e.g., aperture 635), while preventing light from transmitting through the first aperture (e.g., aperture 631). The "active" light emitters for the second period can be the same as the first period or can be different, where the reflection of the "active" light emitters are captured by aperture 635.

A light path can exist between light emitter 606 and light sensor 604, and another light path can exist between light emitter 616 and light sensor 614. The paths can be located such that different areas of the user's skin are intentionally measured. For example, the device can be configured with two light paths with the same separation distances, but different locations. One light path can be associated with an area of the user's skin that has a different level of skin pigmentation or melanin content than the other light path. Device 600 can utilize the measurements from both light paths to extract out the effects that the skin pigmentation or melanin content can have on the PPG signal.

In some examples, the shape of one or more apertures can be changed. In some examples, the shapes of the apertures in device 600 can be different. For example, the shape of aperture 635 can be an oval, whereas the shape of aperture 633 can be circular. The device can adjust the shape of each aperture based on variations in the user's skin at those locations where the light reflects, for example.

In some examples, light emitters 606 and 616 can be different light sources. Exemplary light sources can include, but are not limited to, light emitting diodes (LEDs), incandescent lights, and fluorescent lights. In some examples, light emitters 606 and 616 can have different emission wavelengths. For example, light emitter 616 can be a green LED, and light emitter 606 can be an infrared (IR) LED. A user's blood can effectively absorb more light from a green light source than an IR source. Thus, the light path coupled to light emitter 616, with the shorter separation distance 621, can be used to measure a PPG signal when a user is sedentary, for example. An IR light source can effectively travel further distances through a user's skin than other light sources, so light emitter 606, located the longer distance 623 away from associated light sensor 604, can be used. In some examples, light emitters 606 and 616 can have different emission intensities.

Figure 7:
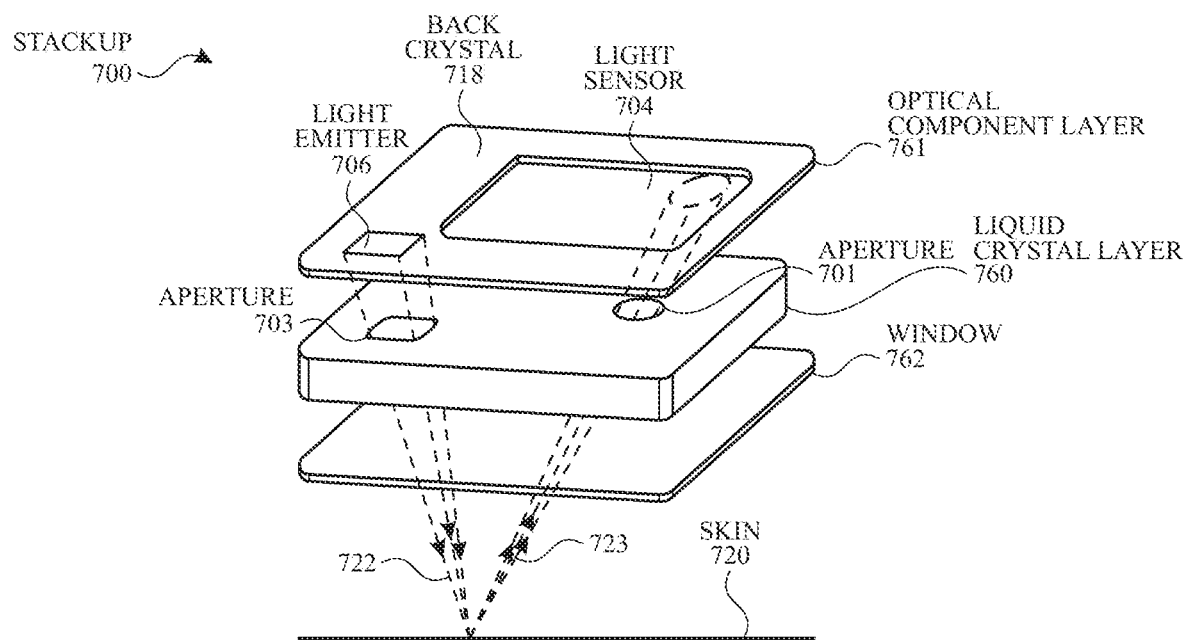
FIG. 7 illustrates a cross-sectional view of a partial stackup of an electronic device capable of dynamically adjusting one or more aperture sizes, one or more path lengths, and one or more aperture shapes through a liquid crystal layer according to examples of the disclosure.

FIG. 7 illustrates a cross-sectional view of a partial stackup of an electronic device capable of dynamically adjusting one or more aperture sizes, one or more path lengths, and one or more aperture shapes through a liquid crystal layer according to examples of the disclosure. Stackup 700 can include an optical component layer 761, a liquid crystal layer 760, and a window 762. Optical component layer 761 can include a light emitter 706 and a light sensor 704, where the active area of both the light emitter 706 and the light sensor 704 can be facing the user's skin 720. In some examples, light emitter 706 and light sensor 704 can be located on different layers. In some examples, optical component layer 761 can include a back crystal 718. Window 762 can be any material or substrate that is at least partially transparent.

Liquid crystal layer 760 can include a liquid crystal material and transparent electrodes. Liquid crystal layer can include components from any type of liquid crystal technology including, but not limited to, in-plane switching (IPS), fringe field switching (FFS), or twisted nematic (TN). Liquid crystal layer 760 can further include a thin-film transistors (TFTs) layer adjacent to the liquid crystal material. Individual sections of the liquid crystal material can variably allow light to pass through when an electric field is applied to the liquid crystal material. The electric field can be generated based upon a voltage difference between the transparent electrodes. For example, a voltage difference can be applied to the sections of the liquid crystal layer 760 located substantially near apertures 701 and 703. Applying the voltage difference substantially near aperture 703 can allow light 722 emitted from light emitter 706 to pass through aperture 703 (i.e., sections of liquid crystal layer 760 that are transparent) and through window 762 towards user's skin 720. The user's skin 720, vasculature, and/or blood can absorb a portion of the light and another portion of the light can reflect back as light 723. Light 723 can transmit through window 762 and aperture 701 (i.e., another or the same section of the liquid crystal layer 760 that is transparent) towards light sensor 704. By controlling whether light can be transmitted through each of the individual sections, the size, number, location, and shape of apertures 701 and 703 can be dynamically changed.

Figure 8:
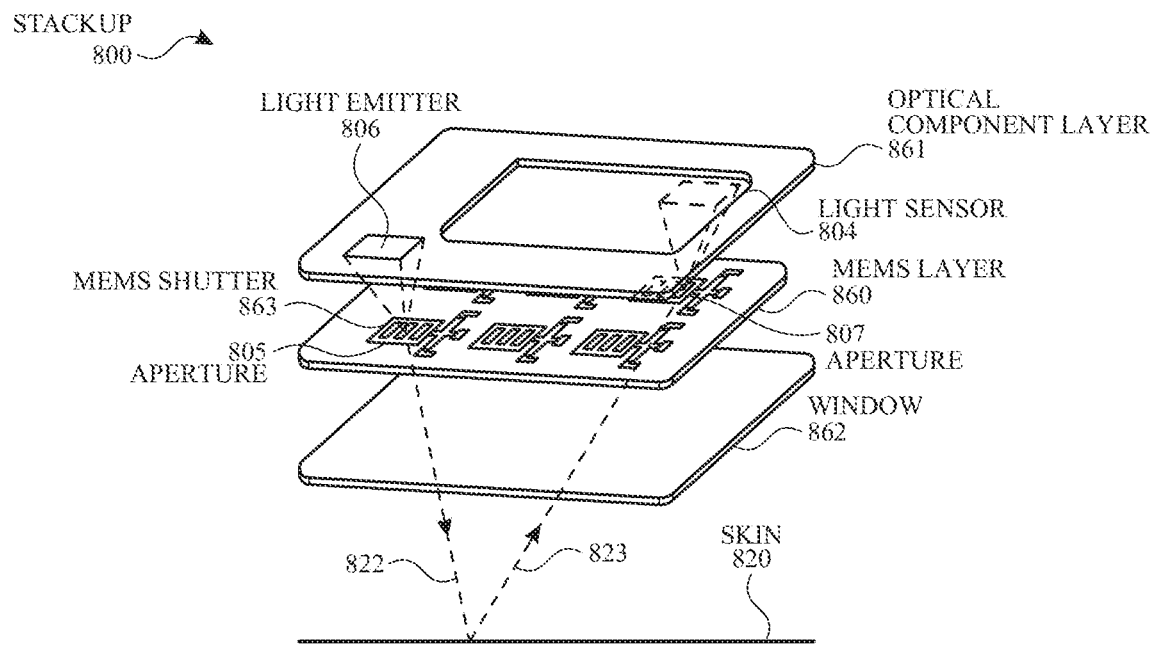
FIG. 8 illustrates a cross-sectional view of a partial stackup of an electronic device capable of dynamically adjusting one or more aperture sizes, one or more path lengths, and one or more aperture shapes through a microelectromechanical systems (MEMS) layer according to examples of the disclosure.

FIG. 8 illustrates a cross-sectional view of a partial stackup of an electronic device capable of dynamically adjusting one or more aperture sizes, one or more path lengths, and one or more aperture shapes through a microelectromechanical systems (MEMS) layer according to examples of the disclosure. Stackup 800 can include an optical component layer 861, a MEMS layer 860, and a window 862. Optical component layer 861 can include a light emitter 806 and a light sensor 804, where the active areas of both the light emitter 806 and the light sensor 804 can be facing the user's skin 820.

MEMS layer 860 can include a plurality of MEMs shutters 863. Each MEMS shutter 863 can either allow or prevent light from passing through, depending on the position of the shutter. The position of each MEMS shutter 863 can be controlled by two lines, where the first line can be a conductive line attached to each shutter. A source (not shown) can provide a current to the first line, which can become electrically attracted to the second line such that the position of the shutter physically moves. Since each MEMS shutter can be coupled to a different source, each MEMS shutter can be individually controlled such that the position of one or more MEMS shutters can allow light to pass through forming apertures 805 and 807, while the position of other MEMS shutters can block light. With aperture 805, the location and amount of the light emitted from the light emitter 806 that is directed towards the user's skin 820 as light 822 can be changed. Similarly, the location and amount of the light 823 that has reflected off the user's skin 820, vasculature, and/or blood and reaches light sensor 804 through aperture 807 can be changed. As a result, the sizes, shapes, and locations of apertures 805 and 807 can be changed. Individual control of the MEMS shutters can be used to tailor device 800 to meet the specific needs of the user, usage condition, and environmental conditions at any given time.

Figure 9:
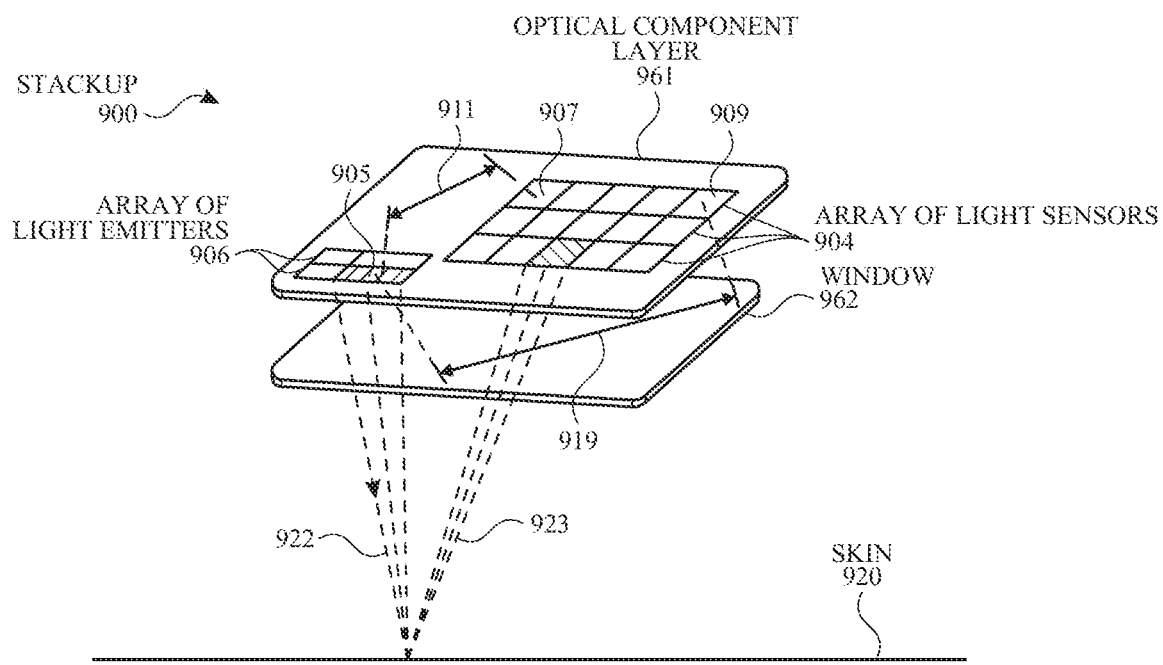
FIG. 9 illustrates a cross-sectional view of a partial stackup of an electronic device capable of dynamically adjusting one or more aperture sizes, one or more path lengths, and one or more aperture shapes through a plurality of individually addressable optical components according to examples of the disclosure.

FIG. 9 illustrates a cross-sectional view of a partial stackup of an electronic device capable of dynamically adjusting one or more aperture sizes, one or more path lengths, and one or more aperture shapes through a plurality of individually addressable optical components according to examples of the disclosure. Stackup 900 can include an optical component layer 961 and a window 962. Optical component layer 961 can include an array of light emitters 906 and an array of light sensors 904. In some examples, optical component layer 961 can include a single light emitter or a single light sensor. Either one or both arrays can include a plurality of individually addressable light emitters or light sensors. The size, location, and shape of the light emitted from the array of light emitters 906 and the size, shape, and location of the light detected by the array of light sensors 904 can be determined by individually addressing the appropriate optical components. Additionally, individually addressing the appropriate optical components can also determine the separation distance between the light emitter and light sensor of a given light path.

For example, the size of the light 922 emitted from the array of light emitters 906 can be increased by increasing the number in the array of light emitters 906 that are addressed (i.e., turned on). To change the location or path length or both, the device can change which light sensor or light emitter (or both) to address. For example, path 911 can be selected by addressing light emitter 905 and light sensor 907. Path 919, different from 911, can be selected by addressing light emitter 905 and light sensor 909. In some examples, stackup 900 can include an array of light sensors, but only one light sensor can be employed. In some examples, stackup 900 can include an array of light emitters, but only one light emitter can be employed.

In some examples, the array of light emitters can include a plurality of individual light emitters. In some examples, the array of light sensors can include a plurality of individual light sensors. In some examples, the light emitters included in the array of light emitters 906 can have different emission properties, such as wavelength and intensity. In some examples, the light sensors included in the array of light sensors 904 can have different sensing properties, such as wavelength and intensity. In some examples, one or both of the light emitters and light sensors can have broadband sensing or emission capabilities. In some examples, the light emitter or light detector or both can be coupled to one or more optical filters. For example, at least one light emitter can be a broadband source. Some of the light emitters included in the array of light emitters can be coupled to a green optical filter, and others of the light emitters included in the array of light emitters can be coupled to an infrared optical filter. In some examples, the light emitter or light detector or both can be coupled to an adjustable diffuse layer, aperture layer, window, mask or filter that selectively allows or blocks light to transmit through.

Figure 10A:
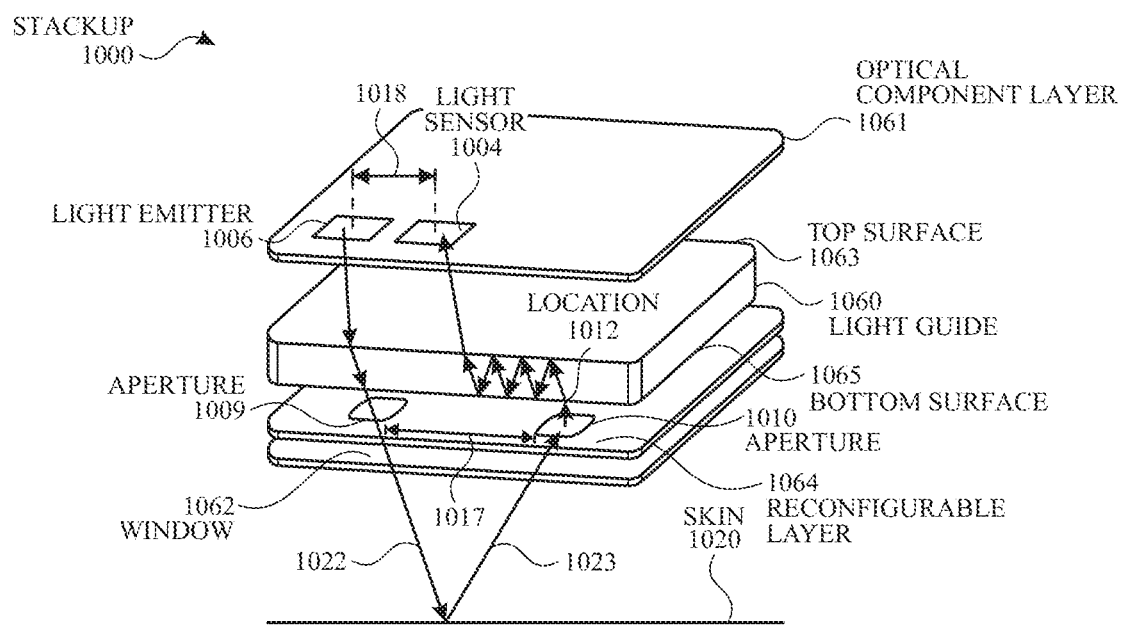
FIG. 10A illustrates a cross-sectional view of a partial stackup of an electronic device capable of dynamically adjusting one or more aperture sizes, one or more path lengths, and one or more aperture shapes through a light guide according to examples of the disclosure.

FIG. 10A illustrates a cross-sectional view of a partial stackup of an electronic device capable of dynamically adjusting one or more aperture sizes, one or more path lengths, and one or more aperture shapes through a light guide according to examples of the disclosure. Stackup 1000 can include an optical component layer 1061, a light guide 1060, a reconfigurable layer 1064, and a window 1062. Optical component layer 1061 can include one or more light emitters, such as light emitter 1006, and one or more light sensors, such as light sensor 1004, such that the active areas are directed towards the user's skin 1020. Both light emitter 1006 and light sensor 1004 can be coupled to light guide 1060.

Light guide 1060 can be a component configured to transport light from one location to another location. As illustrated in the figure, light from the light emitter 1006 can be incident upon top surface 1063 of light guide 1060, can exit out of bottom surface 1065 of light guide 1060, can enter through aperture 1009 located on reconfigurable layer 1064, can transmit through window 1062, and can enter the user's skin 1020 as light 1022. A portion of light can reflect back as light 1023, can transmit through window 1062, can enter through aperture 1010 located on reconfigurable layer 1064, and can enter light guide 1060 at a location 1012 located on the bottom surface 1065 of light guide 1060. Due to total internal reflections, the light hitting each interface of light guide 1060 can reflect back and travel through. In some examples, the reflected light entering into the light guide can be reconfigured (e.g., by controlling the entrance aperture into the light guide 1060 using, for example, a liquid crystal layer, MEMS shutter, etc.) such that the optical distance through the skin is being controlled. Light guide 1060 can transport the reflected light to light sensor 1004. Although light emitter 1006 can be located a distance 1018 away from light sensor 1004, the PPG signal and perfusion index can be determined based on the distance of the light exiting (e.g., light 1022) and the light entering (e.g., light 1023) the device. Since light 1022 exited the device at aperture 1009 and light 1023 entered the device at aperture 1010, separation distance 1017 can be representative of the optical distance through the skin.

Figure 10B:
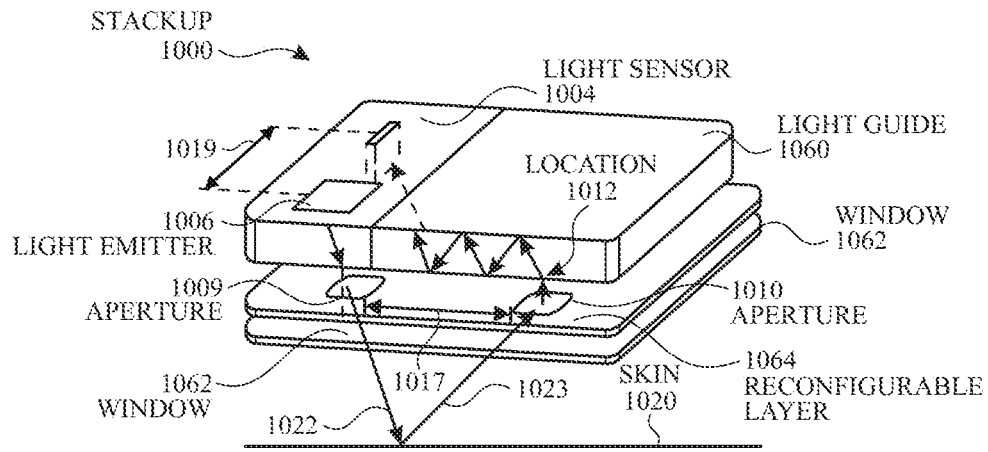
FIG. 10B illustrates a cross-sectional view of a partial stackup of an electronic device capable of dynamically adjusting one or more aperture sizes, one or more path lengths, and one or more aperture shapes through a light guide located on the same layer as the light emitter and light sensor according to examples of the disclosure.

Locating one or more optical components in a location different from the locations where light exits and enters the device can lead to more flexible placement of the optical components. In turn, more flexible placement of the optical components can lead to a thinner, more lightweight portable electronic device. An exemplary configuration is illustrated in FIG. 10B. For example, the light 1022 generated from light emitter 1006 can transmit through aperture 1009 located on reconfigurable layer 1064, can transmit through window 1062, and can be incident upon user's skin 1020. Light sensor 1004 can be an edge-sensing component. Reflected light 1023 can transmit through window 1062, can transmit through aperture 1010 located on reconfigurable layer 1064, and can enter light guide 1060 at location 1012. Light guide 1060 can be configured to allow the reflected light to travel through the light guide and exit out of the edge of the light guide towards the active area of light sensor 1004. In some examples, the reflected light entering into the light guide can be reconfigured (e.g., by controlling the entrance aperture into the light guide 1060 using, for example, a liquid crystal layer, MEMS shutter, etc.) such that the optical distance through the skin is being controlled. Light guide 1060 can transport the reflected light to light sensor 1004. Although light emitter 1006 can be located a distance 1019 away from light sensor 1004, the PPG signal and perfusion index can be determined based on the distance of the light exiting (e.g., light 1022) and the light entering (e.g., light 1023) the device. Since light 1022 exited the device through aperture 1009 and light 1023 entered the device at through aperture 1010, separation distance 1017 can be representative of the optical distance through the skin. With this configuration, light guide 1060, light emitter 1006, and light sensor 1004 can be located on the same layer, eliminating at least one extra layer in the stackup 1000 thereby making the device thinner. In some examples, the light guide 1060 can be a waveguide, one or more lenses, or one or more reflectors.

Although examples of the disclosure illustrate dynamic adjustment using a liquid crystal layer, MEMS shutters, individually-addressable optical components, or a light guide, one skilled in the art would understand that any adjustable window or filter could be used. Examples of the disclosure can include one or more moveable apertures, irises, or windows. Additionally, examples of the disclosure can include adjusting the percentage of transmitted light through one or more apertures.

Figure 11A:
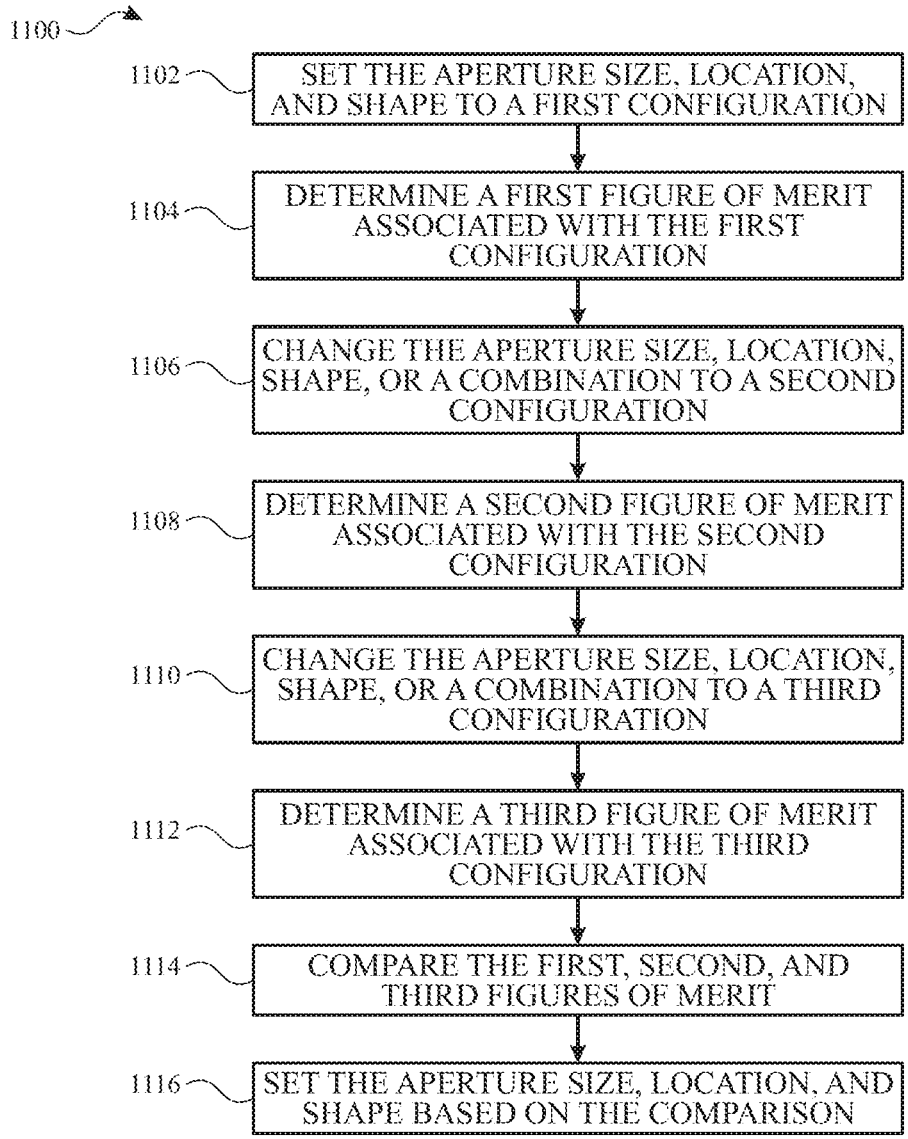
FIGS. 11A-11C illustrate exemplary flow diagrams for a process of dynamically adjusting one or more aperture sizes, one or more path lengths, one or more aperture shapes, or a combination in an electronic device according to examples of the disclosure.
Figure 11B:
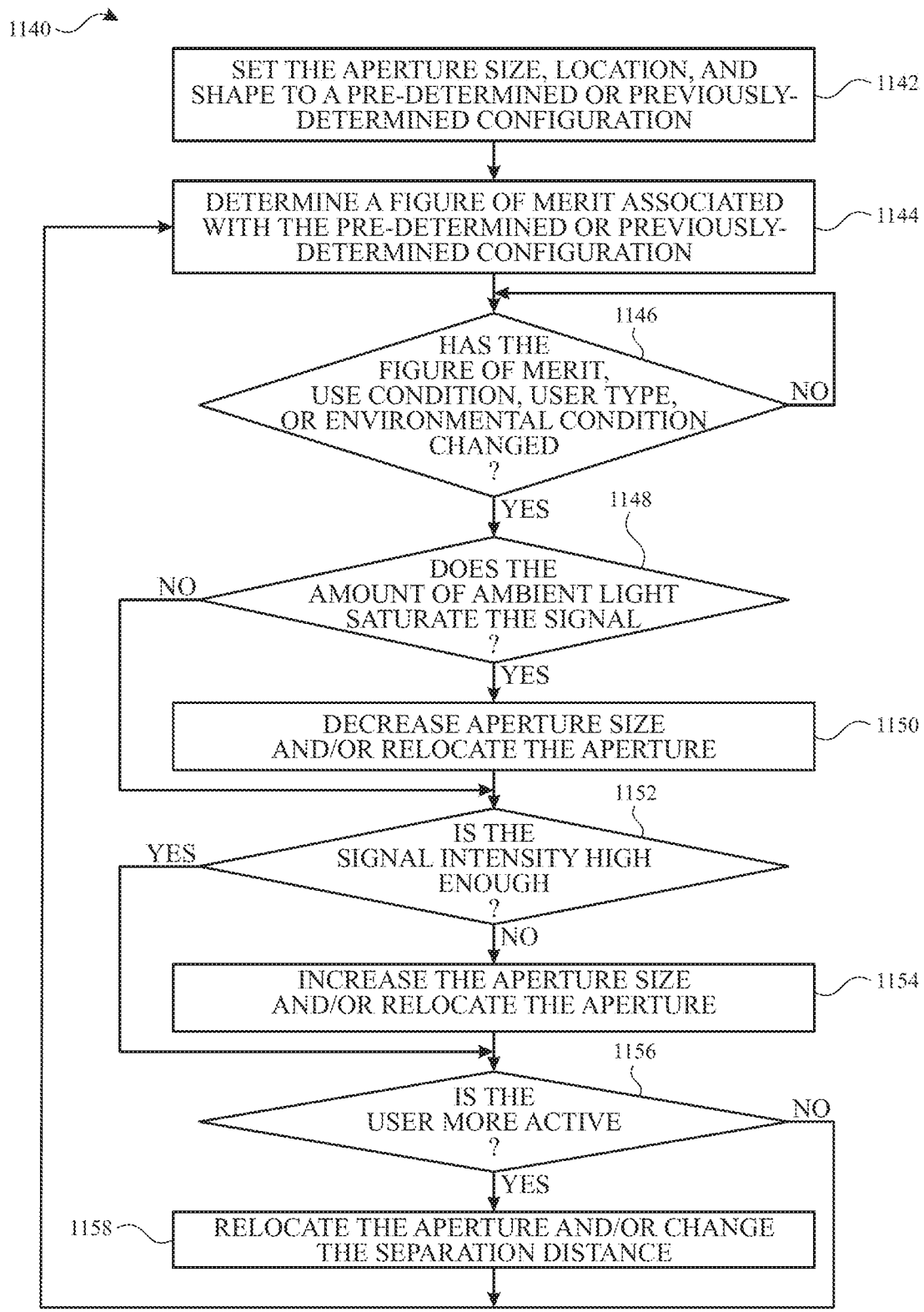
Figure 11C:
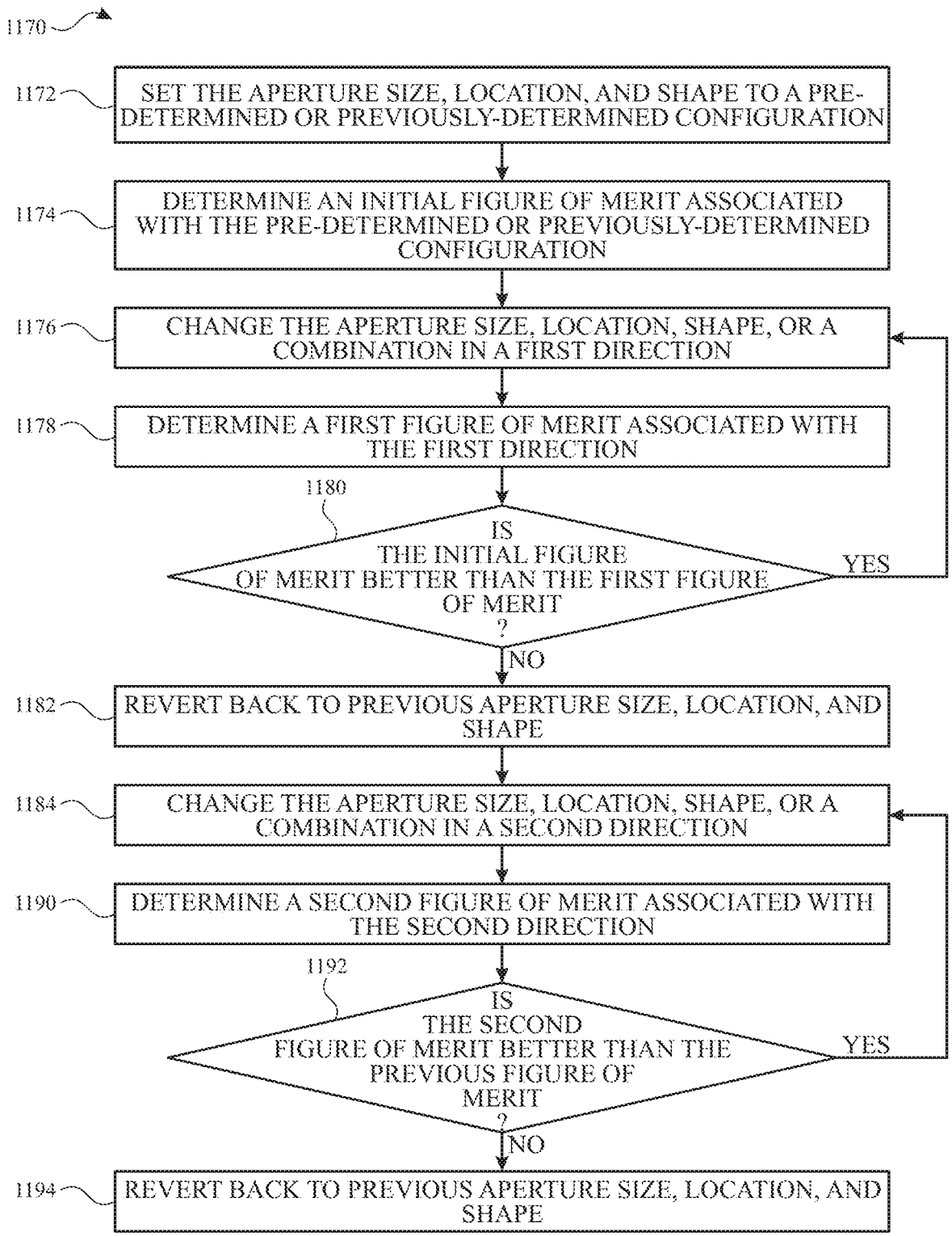

FIGS. 11A-11C illustrate exemplary flow diagrams for a process of dynamically adjusting one or more aperture sizes, one or more path lengths, one or more aperture shapes, or a combination in an electronic device according to examples of the disclosure. Process 1100 can be used as an initial calibration procedure or for a coarse determination of the optimal aperture size, location, and shape, for example. Process 1100 can begin by setting the aperture size, location, and shape to a first configuration (step 1102). A processor or controller coupled to the light sensor can calculate a first figure of merit associated with the first configuration (step 1104). In some examples, the figure of merit can be the signal-to-noise ratio. In some examples, the figure of merit can be the modulated signal intensity, PPG signal value, or perfusion index value. The aperture size, location, shape, or a combination can be changed to a second configuration (step 1106). A second figure of merit associated with the second configuration can be calculated (step 1108). The aperture size, location, shape, or combination can be changed to a third configuration (step 1110). A third figure of merit associated with the third configuration can be calculated (step 1112). The first, second, and third figures of merit can be compared (step 1114), and the aperture size, location, and shape can be set based on the comparison (step 1116).

Process 1140, illustrated in FIG. 11B, can be used to adjust the aperture size, location, and shape while the device is being used by the user and after the calibration procedure, for example. Process 1140 can begin by setting the aperture size, location, and shape to a pre-determined or previously determined configuration (step 1142). A processor or controller can determine a figure of merit associated with the pre- or previously determined configuration (step 1144). The processor can determine whether the figure of merit, use condition, user type, or environmental condition has changed (step 1146). If not, the configuration of the apertures can remain unchanged. If so, the processor can check whether the amount of ambient light saturates the signal (step 1148). If the ambient light levels saturate the signal, the device can decrease the aperture size and/or relocate the aperture until some or all of the ambient light is blocked from reaching the light sensors (step 1150). Alternatively or additionally, the aperture can be relocated to a location where the ambient light levels are lower (e.g., a location further away from the ambient light source). The processor can check if the signal intensity is high enough (step 1152). If the signal intensity is not high enough, the device can increase the aperture size and/or relocate the aperture to allow more reflected light to reach the active area of the light sensors (step 1154). The processor can also check if the user has become more active (step 1156). If the user has become more active, the device can relocate the aperture and/or change the separation distance between the light sensors and light emitters (step 1158). If desired, the processor can repeat the process.

Process 1170, illustrated in FIG. 11C, can be used to adjust the aperture size, location, and shape while the device is being used by the user and after the calibration procedure, for example. In some examples, process 1170 can be used to fine-tune the properties of the one or more apertures. Process 1170 can begin with setting the aperture properties (e.g., size, location, shape, etc.) to a pre-determined or previously determined configuration (step 1172). A processor or controller can determine an initial figure of merit associated with the pre-determined or previously determined configuration (step 1174). The device can change the aperture properties in a first direction (step 1176). A first direction can include, but is not limited to, increasing the size, separation distance, or location of the apertures away from a reference point. A first figure of merit associated with the first direction can be determined (step 1178). The processor can compare the initial figure of merit with the first figure of merit to determine if the change in the first direction is desired (step 1180). If the change in the first direction led to a better figure of merit, then the aperture properties can be continually changed towards the first direction. In some examples, a better figure of merit is one where the initial figure of merit is greater than the first figure of merit. In some examples, a better figure of merit is one where the initial figure of merit is less than the first figure of merit. If the change in the first direction was not favorable, then the device can revert back to the previous aperture properties (step 1182). The device can change the aperture properties in a second direction (step 1184). In some examples, the second direction can be opposite the first direction. The processor can determine a second figure of merit associated with the second direction (step 1190) and can compare the second figure of merit to the previous figure of merit (step 1192). If the second figure of merit is better than the previous figure of merit, then the aperture properties can be continually changed towards the second direction. In some examples, a better figure of merit is one where the second figure of merit is greater than the previous figure of merit. In some examples, a better figure of merit is one where the second figure of merit is less than the previous figure of merit. If the change in the second direction was not favorable, then the device can revert back to the previous aperture properties (step 1194). If there are no changes that result in a more favorable figure of merit, then the optimization process can cease.

In some examples, the processor can adjust the aperture size, location, and shape based on a tracking history. The processor can maintain a record of the user's typical use conditions or environmental conditions and can adjust the aperture based on this record. Although the drawings illustrate process flows for optimizing one aperture size, location, shape, or combination, examples of the disclosure can include optimization for multiple apertures. Examples of the disclosure can include optimization of the number of apertures and consideration of whether an aperture transmits light to multiple components. Additionally, the use of the term "aperture" or "apertures" is meant to include any opening or material where light is selectively allowed to transmit through.

Although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

Figure 12:
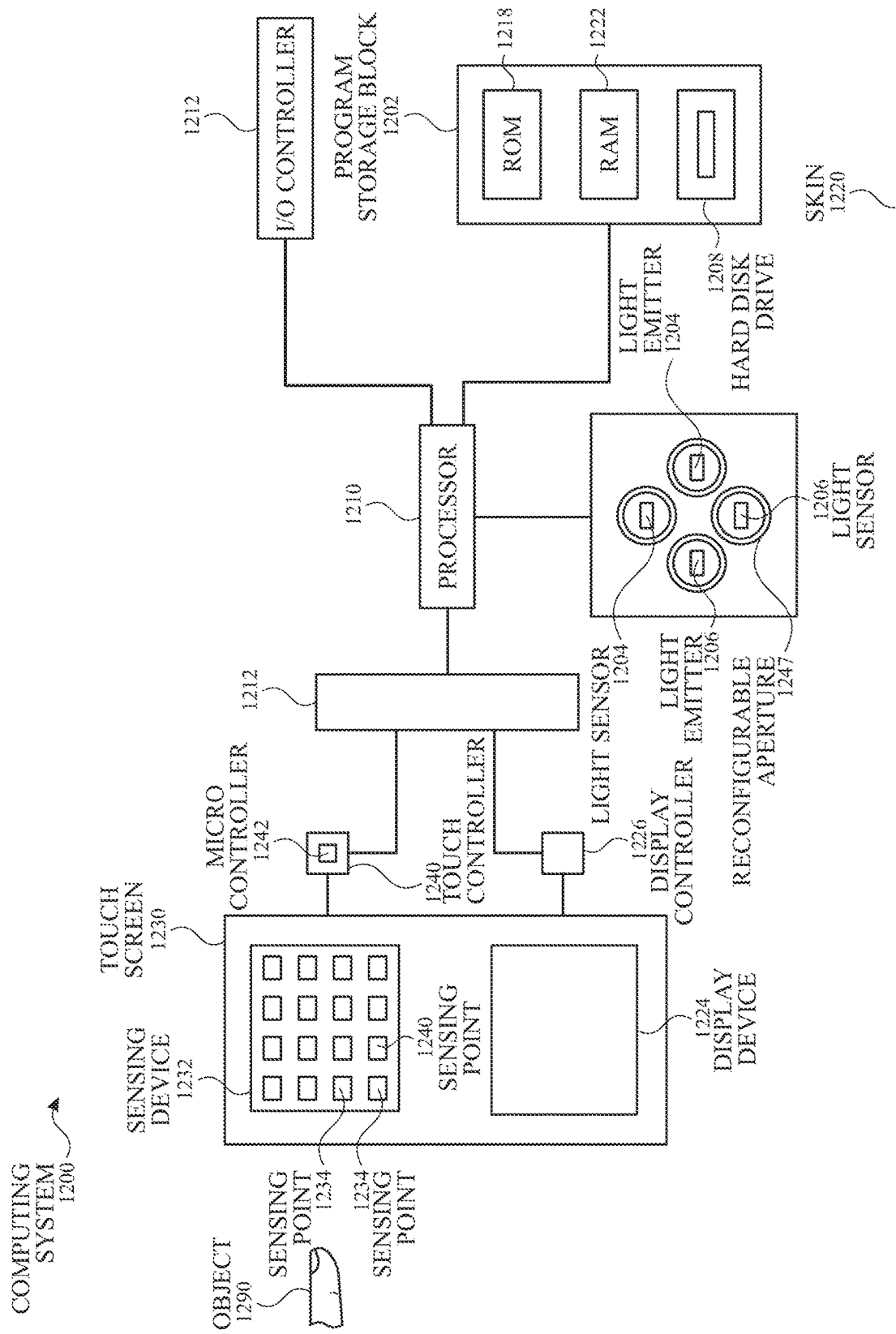
FIG. 12 illustrates an exemplary block diagram of a computing system comprising light emitters and light sensors for measuring a signal associated with a user's physiological state according to examples of the disclosure.

FIG. 12 illustrates an exemplary block diagram of a computing system comprising light emitters and light sensors for measuring a signal associated with a user's physiological state according to examples of the disclosure. Computing system 1200 can correspond to any of the computing devices illustrated in FIGS. 1A-1C. Computing system 1200 can include a processor 1210 configured to execute instructions and to carry out operations associated with computing system 1200. For example, using instructions retrieved from memory, processor 1210 can control the reception and manipulation of input and output data between components of computing system 1200. Processor 1210 can be a single-chip processor or can be implemented with multiple components.

In some examples, processor 1210 together with an operating system can operate to execute computer code and produce and use data. The computer code and data can reside within a program storage block 1202 that can be operatively coupled to processor 1210. Program storage block 1202 can generally provide a place to hold data that is being used by computing system 1200. Program storage block 1202 can be any non-transitory computer-readable storage medium, and can store, for example, history and/or pattern data relating to PPG signal and perfusion index values measured by one or more light sensors such as light sensors 1204. By way of example, program storage block 1202 can include Read-Only Memory (ROM) 1218, Random-Access Memory (RAM) 1222, hard disk drive 1208 and/or the like. The computer code and data could also reside on a removable storage medium and loaded or installed onto the computing system 1200 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 1200 can also include an input/output (I/O) controller 1212 that can be operatively coupled to processor 1210, or it can be a separate component as shown. I/O controller 1212 can be configured to control interactions with one or more I/O devices. I/O controller 1212 can operate by exchanging data between processor 1210 and the I/O devices that desire to communicate with processor 1210. The I/O devices and I/O controller 1212 can communicate through a data link. The data link can be a one-way link or a two-way link. In some cases, I/O devices can be connected to I/O controller 1212 through wireless connections. By way of example, a data link can correspond to PS/2, USB, Firewire, IR, RF, Bluetooth or the like.

Computing system 1200 can include a display device 1224 that can be operatively coupled to processor 1210. Display device 1224 can be a separate component (peripheral device) or can be integrated with processor 1210 and program storage block 1202 to form a desktop computer (e.g., all-in-one machine), a laptop, handheld or tablet computing device of the like. Display device 1224 can be configured to display a graphical user interface (GUI) including perhaps a pointer or cursor as well as other information to the user. By way of example, display device 1224 can be any type of display including a liquid crystal display (LCD), an electroluminescent display (ELD), a field emission display (FED), a light emitting diode display (LED), an organic light emitting diode display (OLED) or the like.

Display device 1224 can be coupled to display controller 1226 that can be coupled to processor 1210. Processor 1210 can send raw data to display controller 1226, and display controller 1226 can send signals to display device 1224. Data can include voltage levels for a plurality of pixels in display device 1224 to project an image. In some examples, processor 1210 can be configured to process the raw data.

Computing system 1200 can also include a touch screen 1230 that can be operatively coupled to processor 1210. Touch screen 1230 can be a combination of sensing device 1232 and display device 1224, where the sensing device 1232 can be a transparent panel that is positioned in front of display device 1224 or integrated with display device 1224. In some cases, touch screen 1230 can recognize touches and the position and magnitude of touches on its surface. Touch screen 1230 can report the touches to processor 1210, and processor 1210 can interpret the touches in accordance with its programming. For example, processor 1210 can perform tap and event gesture parsing and can initiate a wake of the device or powering on one or more components in accordance with a particular touch.

Touch screen 1230 can be coupled to a touch controller 1240 that can acquire data from touch screen 1230 and can supply the acquired data to processor 1210. In some cases, touch controller 1240 can be configured to send raw data to processor 1210, and processor 1210 can process the raw data. For example, processor 1210 can receive data from touch controller 1240 and can determine how to interpret the data. The data can include the coordinates of a touch as well as pressure exerted. In some examples, touch controller 1240 can be configured to process raw data itself. That is, touch controller 1240 can read signals from sensing points 1234 located on sensing device 1232 and can turn the signals into data that the processor 1210 can understand.

Touch controller 1240 can include one or more microcontrollers such as microcontroller 1242, each of which can monitor one or more sensing points 1234. Microcontroller 1242 can, for example, correspond to an application specific integrated circuit (ASIC), which works with firmware to monitor the signals from sensing device 1232, process the monitored signals, and report this information to processor 1210.

One or both display controller 1226 and touch controller 1240 can perform filtering and/or conversion processes. Filtering processes can be implemented to reduce a busy data stream to prevent processor 1210 from being overloaded with redundant or non-essential data. The conversion processes can be implemented to adjust the raw data before sending or reporting them to processor 1210.

In some examples, sensing device 1232 can be based on capacitance. When two electrically conductive members come close to one another without actually touching, their electric fields can interact to form a capacitance. The first electrically conductive member can be one or more of the sensing points 1234, and the second electrically conductive member can be an object 1290 such as a finger. As object 1290 approaches the surface of touch screen 1230, a capacitance can form between object 1290 and one or more sensing points 1234 in close proximity to object 1290. By detecting changes in capacitance at each of the sensing points 1234 and noting the position of sensing points 1234, touch controller 1240 can recognize multiple objects, and determine the location, pressure, direction, speed and acceleration of object 1290 as it moves across the touch screen 1230. For example, touch controller 1290 can determine whether the sensed touch is a finger, tap, or an object covering the surface.

Sensing device 1232 can be based on self-capacitance or mutual capacitance. In self-capacitance, each of the sensing points 1234 can be provided by an individually charged electrode. As object 1290 approaches the surface of the touch screen 1230, the object can capacitively couple to those electrodes in close proximity to object 1290, thereby stealing charge away from the electrodes. The amount of charge in each of the electrodes can be measured by the touch controller 1240 to determine the position of one or more objects when they touch or hover over the touch screen 1230. In mutual capacitance, sensing device 1232 can include a two layer grid of spatially separated lines or wires (not shown), although other configurations are possible. The upper layer can include lines in rows, while the lower layer can include lines in columns (e.g., orthogonal). Sensing points 1234 can be provided at the intersections of the rows and columns. During operation, the rows can be charged, and the charge can capacitively couple from the rows to the columns. As object 1290 approaches the surface of the touch screen 1230, object 1290 can capacitively couple to the rows in close proximity to object 1290, thereby reducing the charge coupling between the rows and columns. The amount of charge in each of the columns can be measured by touch controller 1240 to determine the position of multiple objects when they touch the touch screen 1230.

Computing system 1200 can also include one or more light emitters such as light emitters 1206 and one or more light sensors such as light sensors 1204 proximate to skin 1220 of a user. Light emitters 1206 can be configured to generate light, and light sensors 1204 can be configured to measure a light reflected or absorbed by skin 1220, vasculature, and/or blood of the user. Device 1200 can include dynamically reconfigurable apertures 1247 coupled to light emitters 1206 and light sensors 1204. Light sensor 1204 can send measured raw data to processor 1210, and processor 1210 can perform noise and/or artifact cancelation to determine the PPG signal and/or perfusion index. Processor 1210 can dynamically activate light emitters and/or light sensors and dynamically reconfigure the aperture properties based on an application, user skin type, and usage conditions. In some examples, some light emitters and/or light sensors can be activated, while other light emitters and/or light sensors can be deactivated to conserve power, for example. In some examples, processor 1210 can store the raw data and/or processed information in a ROM 1218 or RAM 1222 for historical tracking or for future diagnostic purposes.

Figure 13:
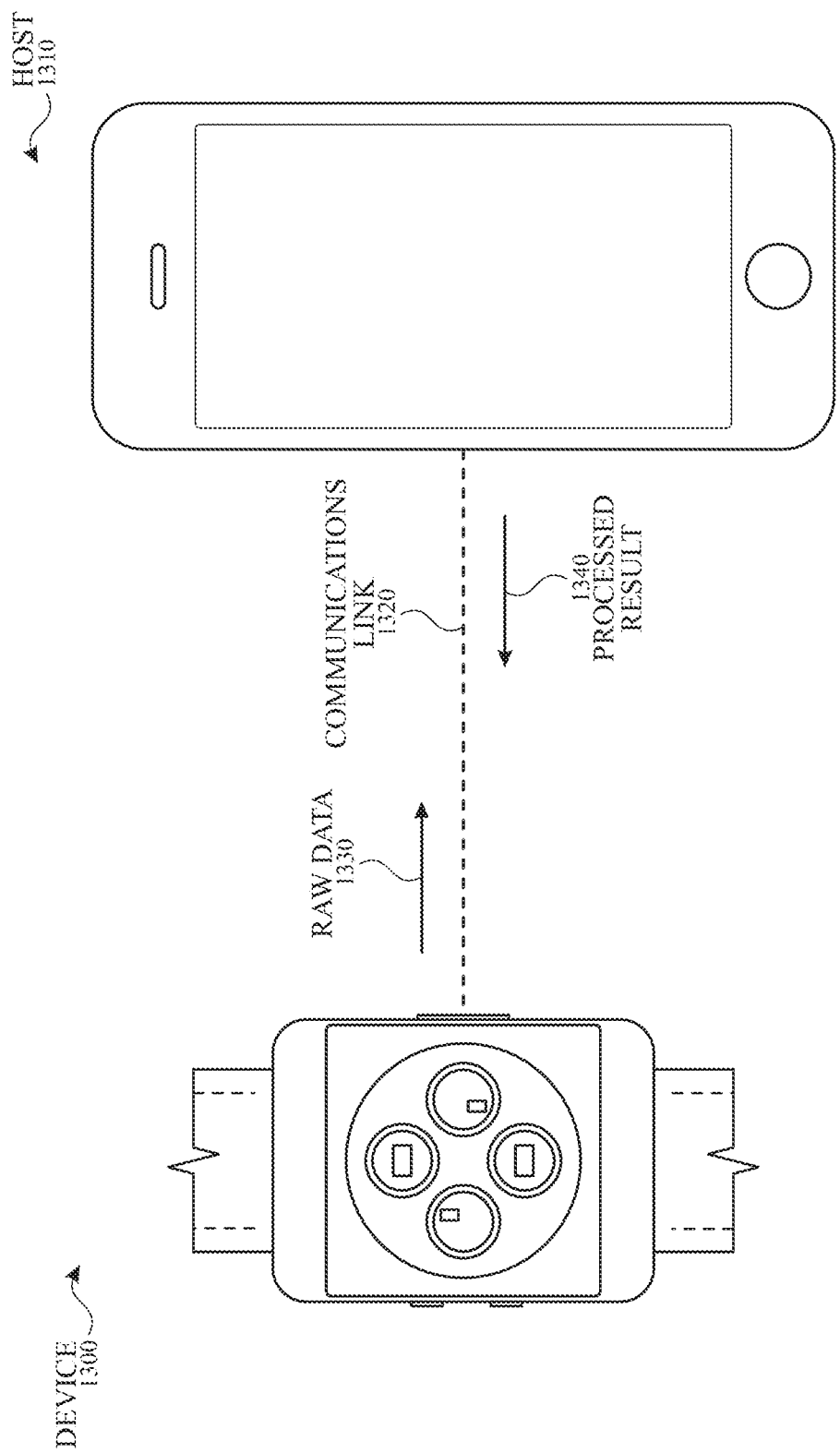
FIG. 13 illustrates an exemplary configuration in which an electronic device is connected to a host according to examples of the disclosure.

In some examples, the light sensors can measure light information and a processor can determine a PPG signal and/or perfusion index from the reflected or absorbed light. Processing of the light information can be performed on the device as well. In some examples, processing of light information need not be performed on the device itself. FIG. 13 illustrates an exemplary configuration in which an electronic device is connected to a host according to examples of the disclosure. Host 1310 can be any device external to device 1300 including, but not limited to, any of the systems illustrated in FIGS. 1A-1C or a server. Device 1300 can be connected to host 1310 through communications link 1320. Communications link 1320 can be any connection including, but not limited to, a wireless connection and a wired connection. Exemplary wireless connections include Wi-Fi, Bluetooth, Wireless Direct and Infrared. Exemplary wired connections include Universal Serial Bus (USB), FireWire, Thunderbolt, or any connection requiring a physical cable.

In operation, instead of processing light information from the light sensors on the device 1300 itself, device 1300 can send raw data 1330 measured from the light sensors over communications link 1320 to host 1310. Host 1310 can receive raw data 1330, and host 1310 can process the light information. Processing the light information can include canceling or reducing any noise due to artifacts and determining physiological signals such as a user's heart rate. Host 1310 can include algorithms or calibration procedures to account for differences in a user's characteristics affecting PPG signal and perfusion index. Additionally, host 1310 can include storage or memory for tracking a PPG signal and perfusion index history for diagnostic purposes. Host 1310 can send the processed result 1340 or related information back to device 1300. Based on the processed result 1340, device 1300 can notify the user or adjust its operation accordingly. By offloading the processing and/or storage of the light information, device 1300 can conserve space and power-enabling device 1300 to remain small and portable, as space that could otherwise be required for processing logic can be freed up on the device.

In some examples, an electronic device is disclosed. The device can comprise: one or more light emitters configured to emit light; one or more light sensors configured to detect a reflection of the emitted light; and a material capable of forming one or more dynamically reconfigurable apertures to allow light to be transmitted from at least one of the one or more light emitters to at least one of the one or more light sensors. Additionally or alternatively to one or more examples disclosed above, in other examples, the electronic device further comprises one or more light paths, each light path associated with one of the one or more light emitters and one of the one or more light sensors, wherein the electronic device is capable of dynamically reconfiguring one or more of a separation distance of the one or more light paths, a size of the one or more dynamically reconfigurable apertures, a location of the one or more dynamically reconfigurable apertures, and a shape of the one or more dynamically reconfigurable apertures. Additionally or alternatively to one or more examples disclosed above, in other examples, one or more optical properties of the material is changed to form the one or more dynamically reconfigurable apertures. Additionally or alternatively to one or more examples disclosed above, in other examples, the material comprises a liquid crystal layer capable of forming the one or more dynamically reconfigurable apertures. Additionally or alternatively to one or more examples disclosed above, in other examples, the material comprises a plurality of microelectromechanical (MEMS) shutters capable of forming the one or more dynamically reconfigurable apertures. Additionally or alternatively to one or more examples disclosed above, in other examples, the material comprises a light guide configured to receive at least one of the emitted light and the reflection of the emitted light. Additionally or alternatively to one or more examples disclosed above, in other examples, at least one of the emitted light and the reflection of the emitted light enters or exits the light guide in a location different from the one or more light emitters or the one or more light sensors. Additionally or alternatively to one or more examples disclosed above, in other examples, the light guide is located on a same layer as at least one of the one or more light emitters and the one or more light sensors. Additionally or alternatively to one or more examples disclosed above, in other examples, the optical properties of the material are different in a location corresponding to the one or more dynamically reconfigurable apertures than a location outside of the one or more dynamically reconfigurable apertures. Additionally or alternatively to one or more examples disclosed above, in other examples, the one or more light sensors includes at least two light sensors capable of sensing different wavelengths. Additionally or alternatively to one or more examples disclosed above, in other examples, the one or more light emitters includes at least two light emitters capable of emitting at different wavelengths. Additionally or alternatively to one or more examples disclosed above, in other examples, the device further comprises: a first light path associated with at least one of the one or more light sensors and at least one of the one or more light emitters and having a first separation distance; and a second light path associated with at least one of the one or more light sensors and at least one of the one or more light emitters and having a second separation distance greater than the first separation distance, wherein a sensing wavelength of the at least one of the one or more light sensors or an emission wavelength of the at least one of the one or more light emitters associated with the second light path is longer than a sensing wavelength of the at least one of the one or more light sensors or an emission wavelength of the at least one of the one or more light emitters associated with the first light path. Additionally or alternatively to one or more examples disclosed above, in other examples, the one or more light emitters are located on a different layer than the one or more light sensors. Additionally or alternatively to one or more examples disclosed above, in other examples, the one or more light emitters are formed from an array of individually addressable light emitters. Additionally or alternatively to one or more examples disclosed above, in other examples, the one or more light sensors are formed from an array of individually addressable light sensors. Additionally or alternatively to one or more examples disclosed above, in other examples, the electronic device further comprises at least one optical filter, wherein at least one of the one or more light emitters is a broadband source coupled to the at least one optical filter.

In some examples, a method of determining a user's physiological state with an electronic device, including one or more light emitters and one or more light sensors, is disclosed. The method can comprise: emitting a first light from the one or more light emitters; receiving a second light by the one or more light sensors, the second light being a reflection of the first light; and dynamically reconfiguring one or more apertures to a first configuration to allow the first light to be transmitted from the one or more light emitters, and to allow the second light to be received at the one or more light sensors. Additionally or alternatively to one or more examples disclosed above, in other examples, the method further comprises associating a light path with one of the one or more light emitters and one of the one or more light sensors, wherein the dynamic reconfiguration of the one or more apertures leads to at least one of a different separation distance between the one or more light emitters and the one or more light sensors, a different size of the one or more apertures, a different location of the one or more apertures, and a different shape of the one or more apertures. Additionally or alternatively to one or more examples disclosed above, in other examples, the method further comprises: emitting a third light from the one or more light emitters; receiving a fourth light by the one or more light sensors, the fourth light being a reflection of the third light; and dynamically reconfiguring one or more apertures to a second configuration to allow the third light to be transmitted from the one or more light emitters, and to allow the fourth light to be received at the one or more light sensors, wherein a separation distance for the first configuration is different from a separation distance different for the second configuration. Additionally or alternatively to one or more examples disclosed above, in other examples, the method further comprises: determining a PPG signal from the first configuration; and determining a perfusion index from the second configuration. Additionally or alternatively to one or more examples disclosed above, in other examples, the one or more apertures of the second configuration block the second light and wherein the one or more apertures of the first configuration block the fourth light. Additionally or alternatively to one or more examples disclosed above, in other examples, the method further comprises: determining an amount of noise from a signal of the second light; and dynamically reconfiguring the one or more apertures to a second configuration when the amount of noise or the signal of the second light is greater than or equal to a first threshold, the second configuration having a lower amount of noise than the first configuration. Additionally or alternatively to one or more examples disclosed above, in other examples, the method further comprises: determining a signal value of the second light; and dynamically reconfiguring the one or more apertures to a second configuration when the signal value of the second light is less than or equal to a second threshold, the signal value of the second light being higher than a signal value of the first light in the first configuration. Additionally or alternatively to one or more examples disclosed above, in other examples, the method further comprises controlling a voltage of a liquid crystal material to dynamically reconfigure the one or more apertures. Additionally or alternatively to one or more examples disclosed above, in other examples, the method further comprises controlling a position of one or more microelectromechanical (MEMS) shutters to dynamically reconfigure the one or more apertures. Additionally or alternatively to one or more examples disclosed above, in other examples, the method further comprises controlling an addressing of one or more individually addressable light emitters to dynamically change properties of one or more light paths, each light path associated with one of the one or more light emitters and one of the one or more light sensors. Additionally or alternatively to one or more examples disclosed above, in other examples, the method further comprises controlling an addressing of one or more individually addressable light sensors to dynamically change properties of one or more light paths, each light path associated with one of the one or more light emitters and one of the one or more light sensors. Additionally or alternatively to one or more examples disclosed above, in other examples, the properties of the one or more light paths include at least one of a separation distance, a size, a location, and a shape. Additionally or alternatively to one or more examples disclosed above, in other examples, the dynamic reconfiguration is based on a user activity. Additionally or alternatively to one or more examples disclosed above, in other examples, the method further comprises: emitting a third light from the one or more light emitters; receiving a fourth light from the one or more light sensors, the fourth light being a reflection of the third light; dynamically reconfiguring one or more apertures to a second configuration to allow the third light to be transmitted from the one or more light emitters, and to allow the fourth light to be received at the one or more light sensors; emitting a fifth light from the one or more light emitters; receiving a sixth light from the one or more light sensors, the sixth light being a reflection of the fifth light; dynamically reconfiguring one or more apertures to a third configuration to allow the fifth light to be transmitted from the one or more light emitters, and to allow the sixth light to be received at the one or more light sensors; and comparing a signal from the second light to a signal from the fourth and sixth light.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. An electronic device for measuring physiological information, the device comprising:
   one or more light emitters that emit light, the one or more light emitters included in one or more optical components;
   one or more light sensors that detect a return of at least a portion of the emitted light, the one or more light sensors included in the one or more optical components;
   a device component capable of forming one or more apertures, the one or more apertures having a configuration to allow light to be transmitted to the one or more optical components, received by the one or more optical components, or both,
   the device component that:
      receives one or more signals, and
      dynamically adjusts, using a controller, one or more properties of at least one of the one or more apertures based on the one or more signals, the one or more properties including a location; and a processor that:
   selects the one or more properties, and
   controls the device component by sending the one or more signals to the device component.

2. The electronic device of claim 1, wherein the device component dynamically adjusts the one or more properties at least in part by a controlling a number of the one or more light emitters that are turned on.

3. The electronic device of claim 1, wherein the device component dynamically adjusts the one or more properties at least in part by controlling a number of the one or more light sensors that are turned on.

4. The electronic device of claim 1, wherein the device component dynamically adjusts the one or more properties by controlling a number of microelectromechanical systems (MEMS) shutters.

5. The electronic device of claim 1, wherein:
   the one or more apertures of a second configuration block light at a location of the light emitted by the one or more light emitters during a first configuration; and
   the one or more apertures of the first configuration block light at a location of the light emitted by the one or more light emitters during the second configuration.

6. The electronic device of claim 1, wherein the one or more signals includes a voltage signal.

7. A method for measuring physiological information, the method comprising:
   emitting light from one or more light emitters, the one or more light emitters included in one or more optical components;
   receiving a return light, the return light including at least a portion of the emitted light by one or more light sensors, the one or more light sensors included in the one or more optical components;
   configuring one or more apertures of a device component to a first configuration, the first configuration allowing light to be transmitted to the one or more optical components, received by the one or more optical components, or both;
   generating one or more control signals indicative of a second configuration; and
   dynamically adjusting, using a controller, one or more properties of at least one of the one or more apertures of the device component to the second configuration, the dynamic adjustment based on the one or more control signals,
   wherein:
      the one or more properties include a location.

8. The method of claim 7, further comprising:
   determining a first figure of merit associated with the first configuration;
   determining a second figure of merit associated with the second configuration;
   dynamically adjusting the one or more properties of at least one of the one or more apertures of the device component to a third configuration;
   determining a third figure of merit associated with the third configuration;
   comparing the first, second, and third figures of merit; and
   setting the one or more properties of at least one of the one or more apertures of the device component to one of the first, second, and third configurations based on the comparison.

9. The method of claim 7, wherein:
   the one or more properties includes a size of the at least one of the one or more apertures of the device component for the second configuration; and
   the size is determined during a calibration procedure.

10. The method of claim 7, further comprising:
   receiving ambient light by the one or more light sensors; and
   determining whether an amount of the received ambient light is greater than a saturation level,
   wherein the dynamic adjustment to the second configuration includes decreasing a size of the at least one of the one or more apertures in accordance with the determination that the amount of received ambient light is greater than the saturation level.

11. The method of claim 7, further comprising:
   determining a first figure of merit associated with the first configuration;
   determining a second figure of merit associated with the second configuration;
   comparing the first figure of merit to the second figure of merit; and
   switching the at least one of the one or more apertures of the device component back to the first configuration based on the comparison.

12. The method of claim 7, further comprising:
   determining one or more signals indicative of the returned light;
   determining whether an intensity of the one or more signals is less than a threshold value,
   wherein the dynamic adjustment includes increasing a size of the at least one of the one or more apertures in the second configuration relative to the first configuration in accordance with the returned light being less than the threshold value.

13. The method of claim 12, wherein the one or more signals include a PPG signal.

14. The method of claim 7, further comprising:
   determining whether a noise associated with the returned light is greater than a threshold value,
   wherein the dynamic adjustment includes decreasing a size of the at least one of the one or more apertures in the second configuration relative to the first configuration in accordance with the noise being greater than the threshold value.

15. The method of claim 7, further comprising:
   determining the physiological information using information from the returned light.

16. The method of claim 7, further comprising:
   executing a calibration procedure as a coarse adjustment;
   wherein the dynamic adjustment of the one or more properties of the at least one of the one or more apertures to the second configuration comprises a fine adjustment.

17. The method of claim 7, wherein the one or more properties of the at least one of the one or more apertures is based on a skin type of a user.

18. The method of claim 7, wherein the location of the at least one of the one or more apertures of the second configuration is different from the first configuration.

19. The method of claim 7, wherein the one or more properties further includes shape, wherein the shape of the at least one of the one or more apertures of the second configuration is different from the first configuration.

* * * * *